(12) United States Patent
Magill et al.

(10) Patent No.: US 7,582,062 B2
(45) Date of Patent: Sep. 1, 2009

(54) METHODS OF NEURAL CENTRE LOCATION AND ELECTRODE PLACEMENT IN THE CENTRAL NERVOUS SYSTEM

(75) Inventors: Peter James Magill, Oxford (GB); John Paul Bolam, Oxford (GB)

(73) Assignee: Medical Research Council, London (GB)

( * ) Notice: Subject to any disclaimer, the term of this patent is extended or adjusted under 35 U.S.C. 154(b) by 444 days.

(21) Appl. No.: 10/939,851

(22) Filed: Sep. 13, 2004

(65) Prior Publication Data

US 2005/0065427 A1   Mar. 24, 2005

Related U.S. Application Data

(60) Provisional application No. 60/502,434, filed on Sep. 12, 2003.

(51) Int. Cl.
*A61B 5/05* (2006.01)
*A61B 5/04* (2006.01)
*A61B 18/18* (2006.01)
*A61N 1/00* (2006.01)

(52) U.S. Cl. .................. 600/554; 600/544; 606/40; 607/2; 607/45; 607/48

(58) Field of Classification Search ................ 600/554, 600/544; 607/45, 48, 2; 606/40
See application file for complete search history.

(56) References Cited

U.S. PATENT DOCUMENTS

| 5,752,979 | A | * | 5/1998 | Benabid | 607/72 |
| 5,769,778 | A | * | 6/1998 | Abrams et al. | 600/14 |
| 6,128,527 | A | * | 10/2000 | Howard et al. | 600/544 |
| 6,330,466 | B1 | * | 12/2001 | Hofmann et al. | 600/378 |
| 2003/0139781 | A1 | * | 7/2003 | Bradley et al. | 607/48 |
| 2004/0147020 | A1 | * | 7/2004 | Freed et al. | 435/368 |
| 2004/0225335 | A1 | * | 11/2004 | Whitehurst et al. | 607/45 |

OTHER PUBLICATIONS

Klostermann et al., Identification of target areas for deep brain stimulation in human basal ganglia substructures based on median nerve sensory evoked potential criteria, J Neurol Neurosurg Psychiatry 2003, 74: 1031-1035.*

Ryan et al., The role of the subthalamic nucleus in the response of globus pallidus neurons to stiumlation of the prelimbic and agranular frontal cortices in rats, 1991, Exp Brain Res, 86: 641-651.*

Maurice et al., Relationships between the Prefrontal Cortex and the Basal Ganglia in the Rat: Physiology of the Corticolsubthalamic Circuits, Nov. 15, 1998, The Journal of Neuroscience, 18(22):9539-9546.*

(Continued)

*Primary Examiner*—Max Hindenburg
*Assistant Examiner*—Emily M Lloyd
(74) *Attorney, Agent, or Firm*—Dann, Dorfman, Herrell & Skillman; Robert C. Netter; Kathleen D. Rigaut

(57) ABSTRACT

A method of locating the position of a selected neural centre in the central nervous system of an animal is disclosed. The method comprises the steps of (a) stimulating neurons at a first central nervous system position; (b) measuring the field potential evoked at a second central nervous system position; and (c) comparing the evoked field potential against a known evoked field potential from the neural centre.

25 Claims, 10 Drawing Sheets

OTHER PUBLICATIONS

Kazakov et al., Unitary responses of the hypothalamic nuclei to stimulation of the frontobasal neocortex, Jan. 1978, Neurophysiology, vol. 10, No. 1, pp. 33-40.*

Klostermann et al—Identification of target areas for deep brain stimulation in human basal ganglia substructures based on median nerve sensory evoked potential criteria., J Neurol Neurosurg Psychiatry 2003; 74, 1031-1035.

Liu et al—The oscillatory activity in the Parkinsonian subthalamic nucleus investigated using the macro-electrodes for deep brain stimulation., Clinical Neurophysiology 113 (2002) 1667-1672.

Liu et al—Localisation of the Subthalamic Nucleus Using Radionics Image FusionTM and StereoplanTM Combined with Field Potential Recording., Stereotact Funct Neurosurg 2001; 76:63-73.

Philip A. Starr—Placement of Deep Brain Stimulators into the Subthalamic Nucleus or Globus pallidus internus: Technical Approach., Stereotact Funct Neurosurg 2002; 79:118-145.

Magill, et al., Synchronous Unit Activity and Local Field Potentials Evoked in the Subthalamic Nucleus by Cortical Stimulation., J. Neurophysiol 92: 700-714, 2004.

Allison, T. et al., "Potentials Evoked in Human and Monkey Cerebral Cortex by Stimulation of the Median Nerve," Brain (1991) 114:2465-2503.

Hanajima, R. et al., "Somatosensory Evoked Potentials (SEPs) Recorded from Deep Brain Stimulation (DBS) Electrodes in the Thalamus and Subthalamic Nucleus (STN)," Clinical Neurophysiology (2004) 115:424-434.

Hubbard, J.I. et al., "Extracellular Field Potentials in the Central Nervous System," In: "Electrophysiological Analysis of Synaptic Transmission," (1969), pp. 265, 270, and 289, Williams and Wilkins, Co., Baltimore.

Lee, E.K. et al., "Generators of Short Latency Human Somatosensory-Evoked Potentials Recorded Over the Spine and Scalp," Journal of Clinical Neurophysiology (1998) 15:227-234.

Logothetis, N. K. et al., "Neurophysiological Investigation of the Basis of the fMRI Signal," Nature (2001) 412:150-157.

Mitzdorf, U. et al., "Current Source-Density Method and Application in Cat Cerebral Cortex: Investigation of Evoked Potentials and EEG Phenomena," Physiological Reviews (1985) 65:37-100.

Wennberg, R.A. et al., "Intracranial Volume Conduction of Cortical Spikes and Sleep Potentials Recorded with Deep Brain Stimulating Electrodes," Clinical Neurophysiology (2003) 114:1403-1418.

* cited by examiner

METHODS OF NEURAL CENTRE LOCATION AND ELECTRODE PLACEMENT IN THE CENTRAL NERVOUS SYSTEM

This application claims priority to U.S. Provisional Application 60/502,434 filed Sep. 12, 2003, the disclosure of which is incorporated herein by reference.

FIELD OF THE INVENTION

The present invention relates to methods of locating the position of a selected neural centre in the central nervous system, to methods of directing an electrode to, and placement at, these neural centres and to treatment of patients in need of treatment by electrical stimulation or electrocoagulation of these neural centres.

BACKGROUND OF THE INVENTION

The basal ganglia (BG) are a group of subcortical brain nuclei in the central nervous system (CNS) that are intimately involved in movement and cognition[17, 27, 26]. The cerebral cortex, the principal afferent of the BG, directly transfers information to the BG via projections to the neostriatum (NS) and subthalamic nucleus (STN). The STN is a small, deep-lying neural centre in the brain that is critical for movement and some cognitive processes. Although not accounted for in classic models of BG function[17, 71], recent studies contend that the input operations of STN are critical for the processing of cortical information in the BG, not least because the corticosubthalamic pathway represents the swiftest route by which the cortex can influence the activity of STN and its targets, the globus pallidus (GP) and the output nuclei of the BG[51, 57].

'Deep brain stimulation' (DBS) or electrocoagulation, by the use of metal electrodes implanted temporally or permanently in the basal ganglia, have been shown to be effective treatments for epilepsy, dystonia and all major symptoms of Parkinson's disease (PD)[41]. Essential tremor and parkinsonian tremor can be ameliorated or even abolished by DBS electrical stimulation of the ventral intermediate nucleus (VIM). In PD, DBS of the STN reduces rigidity, tremor and hypokinesia. A prerequisite for a beneficial outcome of patients is the accurate identification of the position of a chosen target nucleus, usually in the basal ganglia or ventral thalamus, so that special emphasis is to be put on procedural aspects of electrode placement[34].

Whereas DBS techniques utilise electrical currents to stimulate the target neural centre, electrocoagulation techniques involve the supply of electrical currents to heat the neural centre, effectively burning out the neural centre and destroying its activity.

The accepted method for implantation and positioning of DBS macro-electrodes in the STN comprises an initial imaging step, typically magnetic resonance imaging (MRI)-guided stereotactic localisation, followed by confirmation of the motor territory of the target nucleus by micro-electrode mapping[68] and verification of the efficacy of stimulation by trial run.

Whilst MRI and other imaging techniques can provide general information on the location of anatomical structures in a given individual, these techniques often cannot provide detailed information on the exact spatial location of specific neural centres in the BG and, the CNS in general.

Thus to date, high-resolution micro-electrode measurements are used to depict target-specific neuronal discharge patterns of single neurons (aka 'single units'). The micro-electrode measurements are then used to direct the implantation and positioning of the DBS macro-electrode. High standards of technical equipment and practitioner expertise are required to perform these micro-recordings, both of which are not easily available. Moreover, the use of fine micro-electrodes carries an increased risk of neuronal tissue damage by puncture of blood vessels and neurons during implantation of the micro-electrode.

Thus, the surgical implantation of the requisite electrodes for DBS treatment remains seriously disadvantaged by the difficulties associated with unequivocally identifying the STN itself (i.e. distinguishing the STN from surrounding structures) and, once identified, locating the (motor) area of STN that is most useful for subsequent electrical manipulation.

Micro-electrode measurements are designed to record the activity of single units, which may provide limited, but often characteristic, information as to the position of the electrode and thus, the location of the neural centre of interest. In contrast, field potentials (FPs) measure the activity generated by larger groups of firing neurons.

Field potentials may be generated spontaneously or may be evoked by a stimulus. The nature of the FPs evoked by stimulation is critically dependent on the structure that is itself stimulated. Somatosensory evoked field potentials (SEP) have been recorded in the STN during implantation surgery using the DBS-type macro-electrodes[34]. SEPs were generated by stimulation of neurons external of the CNS, specifically at the median nerve in the forearm. The low-amplitude and complex profiles of SEPs recorded along STN trajectories precluded the use of these field potentials for identifying STN targets.

Responses of STN neurons to cerebral cortical input are often 'multiphasic' and vary according to the differential activation of several distinct BG circuits, including the NS and the reciprocally-connected STN-GP network[25, 48, 56, 35]. The complex interactions within cortical and basal ganglia circuits make the theoretical extrapolation of single neuron responses, as measured using micro-electrode techniques, to the population level a difficult task.

Accordingly a number of technical difficulties and problems exist in the unequivocal identification of a neural centre in the CNS. In particular, the inaccuracies associated with current methods for identifying the position of neural centres in the BG, such as the STN, and GP provides a significant obstacle to the treatment of patients by electrode-based therapies, such as DBS and electrocoagulation.

SUMMARY OF THE INVENTION

To gain a better understanding of the degree of synchrony imposed upon the STN and associated neuronal networks by the cerebral cortex, the inventors recorded responses of single units and pairs of neighbouring neurons in the STN to focal electrical stimulation of the ipsilateral frontal cortex in anaesthetised rats. When the subthreshold and suprathreshold activities of groups of neurons are sufficiently synchronised, it is evident at the level of the local field potential (LFP)[30, 53]. Subsequently, the inventors simultaneously recorded the LFPs evoked with the unit response and demonstrated that the unit activity and LFPs in STN can be synchronized to a high level and in a stereotyped manner by cortical input.

Stimulation of ipsilateral frontal cortex evoked synchronous, 'multiphasic' responses in neighbouring units in rostral STN, consisting of, in turn, a brief, short-latency excitation, a brief inhibition, a second excitation and a long-duration inhibition. Evoked LFPs in STN consistently mirrored unit responses; brief, negative deflections in the LFP coincided with excitations, and brief, positive deflections with inhibitions. This characteristic LFP was not related to evoked cortical potentials or fluctuations in ongoing forebrain activity, nor was it observed in structures surrounding STN. The short-latency excitation and associated LFP deflection exhibited the highest fidelity to cortical input.

These data demonstrate that the responses of populations of STN neurons to direct cortical input are locally synchronous and are characteristic of this neural centre.

Synchronised activity is dependent on topography and the intensity of input. The stereotypical profile of the LFP demonstrates utility for locating the STN in clinical as well as non-clinical settings.

The inventors have shown that stimulation of STN afferents, i.e. the brain regions connected to STN, can be used in combination with electrophysiological recording methods to unambiguously identify the STN, and specific regions within it. In particular, selective stimulation of the cerebral cortex, an important STN afferent, has been demonstrated to evoke complex and unique electrical field potentials in STN.

These evoked field potentials are relatively quick and easy to record in the brain and, critically, can be recorded intraoperatively.

Taken together, the inventors have shown that stimulation of structures within the CNS itself, for example, the cerebral cortex, can generate specific FPs in the BG and that characteristic FPs evoked by CNS stimulation can be used to accurately identify these neural centres in a clinical setting, e.g. during the surgical implantation of DBS-type or electrocoagulation-type electrodes.

Accurate identification of the position of CNS neural centres, particularly those of the brain, is required for successful implantation of DBS electrodes necessary if the DBS treatment is to be effective. Direct stimulation of CNS structures evokes characteristic LFPs in selected neural centres which can be measured using the DBS-type macro-electrodes or, alternatively, other implanted micro-electrodes. Analysis of the evoked LFP and comparison against a known, experimentally determined, LFP that is characteristic of the neural centre of interest permits adjustment and refinement, i.e. a fine tuning, of the electrode position until the recorded LFP profile corresponds to the experimentally determined LFP profile (within an accepted set of statistical error tolerances), indicating that the point of measurement on the electrode, typically the electrode tip, is located in the neural centre of interest.

The use of evoked LFPs to accurately identify the location of neural centres of the CNS in a given patient provides for a more accurate placement of DBS or coagulation electrodes and thus, improved therapeutic potential of the DBS treatment by combating some of the major disadvantages associated with surgical intervention as a treatment for Parkinson's disease, dystonia and epilepsy. The methods provided by the inventors thus improve the available treatments for patients exhibiting PD, PD-like or epileptic symptoms, including tremor, or other motor dysfunctions.

The inventors have demonstrated that LFPs evoked in the CNS by direct stimulation of other structures in the CNS can be measured and used as electrophysiological fingerprints to identify specific neural centres.

Field potentials, such as LFPs, provide robust and representative electrophysiological data that can be easily and quickly acquired during or after electrode implantation. Furthermore, because the LFP can be recorded using the therapeutic electrode(s), the risk of neuron damage, and chances of failure of the operation and therapy are reduced.

The inventors have thus provided methods of location of selected CNS neural centres, methods of directing electrodes to, and electrode placement at, these centres leading to improved methods of treatment of patients in need of treatment by DBS or electrocoagulation.

As the LFP evoked at a known neural centre provides an electrophysiological fingerprint, the comparison of the measured LFP during electrode implantation can be automatically compared against the known or standard LFP for a given neural centre. This comparison process may be implemented by provision of computer software. The comparison of LFPs evoked at close anatomical positions, e.g. adjacent nuclei, also enables identification of neural centres for which a characteristic positive LFP signal is not produced. For example, the inventors did not observe the same characteristic LFP response in the zona incerta, the cerebral peduncle and the internal capsule as compared to that in the STN. However, a characteristic drop-off in the evoked signal may be used to identify these structures relative to the position of an adjacent nucleus already identified by a characteristic positive response. Thus, an initial electrode localisation step may be performed to locate a neural centre in which a characteristic positive FP is evoked, e.g. the STN, and then the electrode position may be varied slightly to adjacent neural centres, measurement of the change in evoked FP upon stimulation indicating the position of the electrode at a second neural centre.

Having made initial preparations for the surgical implantation of therapeutic electrodes by arranging the stimulation device, e.g. electrode(s), in position in or adjacent to the cortex, and having made an initial implantation of a micro-electrode or DBS-type macro-electrode in the basal ganglia by MRI-based location, the stimulation of the cerebral cortex, measurement of the LFP evoked and comparison of the evoked LFP with the known evoked LFP can be implemented by a computer programmed with a program for stimulation, measurement of LFP and comparison of the recorded LFP with a selected standard LFP.

The computer program can be further arranged to analyse the recorded LFP within a set of analysis parameters (e.g. amplitudes of positive and/or negative deflections, latencies of responses) input by the practitioner. If the recorded LFP is outside the given parameters, the computer program is operable to control a stepper motor or other device to advance or retract the measuring electrode to adjust its position in the basal ganglia before repeating the stimulation, measurement and comparison cycle. Any such computer controlled arrangement would also permit practitioner input to enable an override, for example, when manually adjusting electrode position.

At its most general the present invention provides for the identification of neural centres in the CNS by measurement of field potentials by stimulation in other CNS structures.

Preferred features of the following aspects may be appropriately combined with any other aspects of the invention.

According to a first aspect of the present invention there is provided a method of locating the position of a selected neural centre in the central nervous system of an animal comprising the steps of:
 a) stimulating neurons at a first central nervous system position;
 b) measuring the field potential evoked at a second central nervous system position; and
 c) comparing the evoked field potential against a known evoked field potential from said neural centre.

The method preferably further comprises repeating steps a-c for one or a plurality of cycles, wherein in each subsequent cycle the position of measurement in step b) is adjusted, until the evoked field potential corresponds to said known evoked field potential. Steps a) and b) are preferably performed simultaneously or in immediate consecutive order.

Preferably the neural centre is a nucleus of the basal ganglia or ventral thalamus, more preferably one of the subthalamic nucleus; the rostral subthalamic nucleus; the caudal subthalamic nucleus; a 'somatomotor' region of the subthalamic nucleus; the zona incerta; the globus pallidus (internal and/or external segments) or the substantia nigra. Alternatively, the neural centre may be a part of the dorsal thalamus e.g. the ventral intermediate nucleus.

Preferably, the first central nervous system position is in the cerebral cortex of the brain, preferably the ipsilateral frontal or pre-frontal cortex, more preferably the motor, pre-motor or somatosensory cortex.

The second central nervous system position is preferably in the basal ganglia or ventral thalamus of the brain and is more preferably within a selected substructure identified by imaging the brain, e.g. by magnetic resonance imaging, radiography or ventriculography, in an imaging step performed before the stimulating step. The selected substructure is preferably one of: the subthalamic nucleus; the rostral subthalamic nucleus; the caudal subthalamic nucleus; a 'somatomotor' region of the subthalamic nucleus; the zona incerta; the globus pallidus (internal and/or external segments) or the substantia nigra. Alternatively, the second central nervous system position may be a part of the dorsal thalamus e.g. the ventral intermediate nucleus.

The measurement of field potential is preferably recorded by at least one electrode inserted into the central nervous system, the electrode may be a therapeutic electrode, preferably a DBS-type macro-electrode, micro-electrode or electrocoagulation electrode.

The stimulation of step a) may be a direct, electrical stimulation using one or more electrodes implanted in the cerebral cortex wherein stimulation is by direct application of electric currents through the electrodes implanted in the CNS.

In an alternative arrangement, the stimulation of step a) may be achieved by the non-invasive stimulation of neurons. This may involve transcranial (also called transcutaneous) electrical stimulation (TES) or transcranial magnetic stimulation.

A TES electrode does not necessarily penetrate into the body of the cortex, but may rest on top of the cortex, on the cortical membranes, or on the scalp itself. Such an electrode may therefore be implanted in, or be positioned in, on, or over, the cerebral cortex.

The stimulation step a) may, therefore, involve direct application, or induction, of electrical currents through electrodes in contact with the CNS, its associated membranes, or the scalp.

Preferably, the evoked event or activity that is to be measured and compared is a local field potential (LFP).

According to a second aspect of the present invention there is provided a method of directing an electrode to a position in a selected neural centre in the central nervous system of an animal comprising the steps of:

i) stimulating neurons at a first central nervous system position;
ii) measuring the field potential evoked at an electrode located at a second central nervous system position;
iii) comparing the evoked field potential against a known evoked field potential from said neural centre.

The method of directing an electrode preferably further comprises repeating steps i-iii for one or a plurality of cycles until the evoked field potential corresponds to said known evoked field potential, wherein between subsequent cycles the evoked field potential is analysed and the position of measurement in step ii) is adjusted to optimise the correspondence between the evoked and known field potentials in the subsequent cycle.

In one preferred arrangement the measuring electrode and directed electrode comprise a single DBS-type macro-electrode which is being directed to a selected neural centre (to subsequently deliver the therapeutic stimulation). As an alternative, measurement of LFPs may be performed using one or more implanted microelectrodes to determine the correct position for insertion of the DBS electrode, which is implanted to that optimal position in a subsequent step.

Suitably, a computer program for carrying out the method of directing an electrode to a position in a selected neural centre as set out in the second aspect is also provided. Optionally, the computer program may only carry out step iii).

A data carrier having a program saved thereon for carrying out the method of directing an electrode to a position in a selected neural centre as set in the second aspect is also preferably provided. Optionally, the data carrier may only have a program saved thereon for performing step iii).

Preferably, a computer programmed to carry out the method of directing an electrode to a position in a selected neural centre as set out in the second aspect is also provided. Optionally, the computer may be programmed to carry out only step iii).

In a third aspect of the present invention there is provided a method of locating the position of the subthalamic nucleus in the central nervous system of an animal comprising the steps of:

a) stimulating neurons of the cerebral cortex;
b) measuring the field potential evoked at a position in the brain;
c) comparing the evoked field potential against a known evoked field potential from the subthalamic nucleus.

Preferably, the animal is an individual selected from the group consisting of:

non-human animals, preferably vertebrates, e.g. rabbit, guinea pig, rat, mouse or other rodent (including any animal in the order Rodentia), cat, dog, pig, sheep, goat, cattle, horse, non-human primate or any non-human mammal; and/or a human.

In a fourth aspect of the present invention there is provided a method of treating a patient in need of treatment by electrical stimulation of a selected neural centre comprising positioning a stimulating electrode at said neural centre, wherein the position of said neural centre in the central nervous system of the patient is determined by:

a) stimulating neurons at a first central nervous system position;
b) measuring the field potential evoked at a second central nervous system position; and
c) comparing the evoked field potential against a known evoked field potential from said neural centre.

The electrical stimulation of the fourth aspect preferably comprises deep brain stimulation.

In a fifth aspect of the present invention there is provided a method of treating a patient in need of treatment by electrocoagulation of a selected neural centre comprising positioning an electrocoagulation electrode at said neural centre, wherein the position of said neural centre in the central nervous system of the patient is determined by:

a) stimulating neurons at a first central nervous system position;

b) measuring the field potential evoked at a second central nervous system position; and c) comparing the evoked field potential against a known evoked field potential from said neural centre.

Preferably in the fifth aspect electrocoagulation is achieved at the selected neural centre by applying an electrical current through said electrode.

In a sixth aspect of the present invention there is provided a method of treating a patient exhibiting a Parkinson's disease, or Parkinson's disease-like, motor dysfunction by electrical stimulation or electrocoagulation of the subthalamic nucleus comprising positioning an electrode at a position in the subthalamic nucleus, wherein the position of the subthalamic nucleus in the central nervous system is determined by:

a) stimulating neurons of the cortex;

b) measuring the field potential evoked at a position in the basal ganglia;

c) comparing the evoked field potential against a known evoked field potential from the subthalamic nucleus.

Preferably, the electrical stimulation method of the sixth aspect is a deep brain stimulation method.

In a seventh aspect of the present invention there is provided a method of treating a patient exhibiting epileptic, or epilepsy-related, dysfunction by electrical stimulation or electrocoagulation of the subthalamic nucleus comprising positioning an electrode at a position in the subthalamic nucleus, wherein the position of the subthalamic nucleus in the central nervous system is determined by:

a) stimulating neurons of the cortex;

b) measuring the field potential evoked at a position in the basal ganglia;

c) comparing the evoked field potential against a known evoked field potential from the subthalamic nucleus.

In a eighth aspect of the present invention there is provided a method of treating a patient exhibiting motor and/or cognitive dysfunction by electrical stimulation or electrocoagulation of the zona incerta comprising positioning an electrode at a position in the zona incerta, wherein the position of the zona incerta in the central nervous system is determined by:

a) stimulating neurons of the cortex;

b) measuring the field potential evoked at a position in the brain;

c) comparing the evoked field potential against a known evoked field potential from the zona incerta.

Methods according to any of the aspects of the invention may be carried out by an appropriately encoded computer program. A computer programmed with such a computer program and a disk or other data carrier having the program saved thereon are also preferably provided.

Neural centre, as used in this specification, relates to an anatomical cluster or group of neurons, often referred to as a nucleus or ganglia, which are commonly related in function. A neural centre may be formed by a functional and/or anatomical substructure of a larger nucleus or ganglia. Examples of neural centres include the basal ganglia, subthalamic nucleus, rostral subthalamic nucleus, caudal subthalamic nucleus, 'somatomotor' subthalamic nucleus, zona incerta, globus pallidus, or substantia nigra.

Central nervous system, as used in this specification, relates to nervous and non-nervous tissue of the brain and spinal column.

Field potential, as used in this specification, relates to the potential difference (or voltage) arising from the simultaneous flow of electrical currents across the axons, dendrites and cell bodies of many cells. Also known as local field potentials or local potentials, field potentials are considered to represent cellular input and output activity on a larger scale when compared to single unit activity (i.e. the potential difference derived from the action potentials of a single cell). Accordingly, field potentials reflect the coordinated activity of a population (or field) of cells. Field potentials are ideally recorded from the extracellular space surrounding cells and are preferably filtered to remove unwanted artefacts or single unit activity.

Aspects and embodiments of the present invention will now be illustrated, by way of example, with reference to the accompanying figures. Further aspects and embodiments will be apparent to those skilled in the art. All documents mentioned in this text are incorporated herein by reference.

DETAILED DESCRIPTION OF THE BEST MODE OF THE INVENTION

Figure 1:
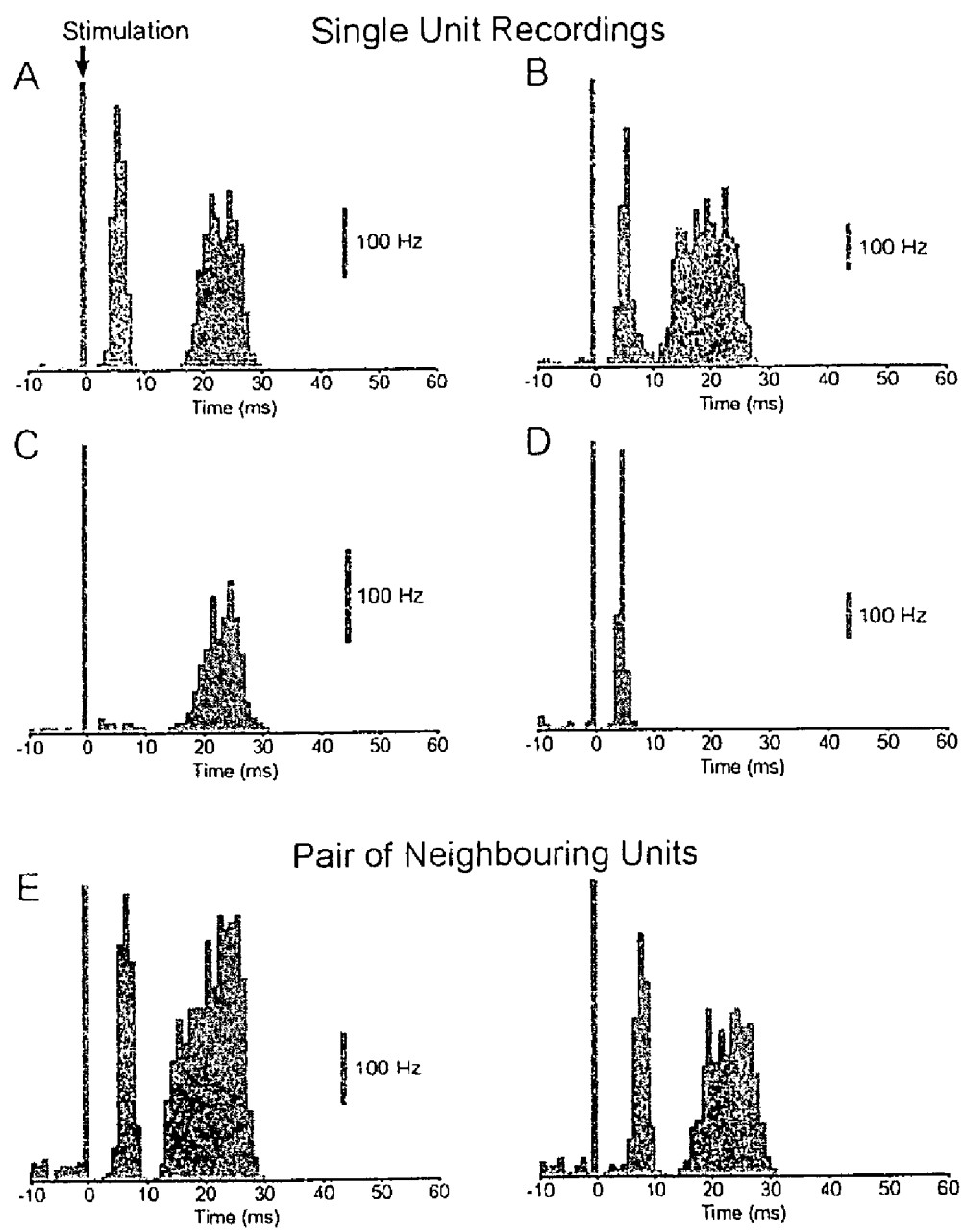
FIG. 1. The responses of neurons in the rostral half of subthalamic nucleus to stimulation of the ipsilateral frontal cortex are often multiphasic and synchronised. Peristimulus time histograms of the responses of single subthalamic nucleus (STN) neurons to frontal cortical stimulation (300 µA) are shown. In this and subsequent figures, stimulation occurred at time zero. (A) Typical 'multiphasic' unit response, which consisted of a short-latency brief excitation, a short-latency brief inhibition, a long-latency excitation and, finally, a long-latency, long-duration inhibition. (B) The two excitation peaks displayed by some neurons were separated by a marked reduction in firing, rather than a significant period of inhibition, during which firing ceased. (C, D) The responses of a small number of neurons included only select phases of the stereotypical response e.g. no short-latency excitation (C), or a short-latency excitation followed by a long-lasting inhibition (D). (E) Responses of two neighbouring STN neurons that were simultaneously recorded using the same electrode. Note that the response profiles were qualitatively similar and that the excitations and inhibitions of both neurons were synchronised. Calibration bar in the left panel of (E) also applies to the right panel. Stimulation artefacts in each panel were truncated for clarity.

Specific details of the best mode contemplated by the inventors for carrying out the invention are set forth below, by way of example. It will be apparent to one skilled in the art that the present invention may be practiced without limitation to these specific details.

Materials and Methods

Electrophysiological Recordings and Labeling of Recording Sites

Experimental procedures were carried out on adult male Sprague-Dawley rats (Charles River, Margate, UK) and were conducted in accordance with the Animals (Scientific Procedures) Act, 1986 (UK) and the European Communities Council Directive (86/609/EEC).

Electrophysiological recordings were made in 13 rats (230-350 g). Anaesthesia was induced with isoflurane (Isoflo™, Schering-Plough Ltd., Welwyn Garden City, UK) and maintained with urethane (1.3 gkg$^{-1}$, i.p.; ethyl carbamate, Sigma, Poole, UK), and supplemental doses of ketamine (30 mgkg$^{-1}$, i.p.; Ketaset™, Willows Francis, Crawley, UK) and xylazine (3 mgkg$^{-1}$, i.p.; Rompun™, Bayer, Germany), as described previously[46]. All wound margins were infiltrated with the local anaesthetic, bupivacaine (0.75% w/v; Astra, Kings Langley, UK), and corneal dehydration was prevented with application of Hypromellose eye drops (Norton Pharmaceuticals Ltd., Harlow, UK). Animals were then placed in a stereotaxic frame. Body temperature was maintained at 37±0.5° C. with the use of a homeothermic heating device (Harvard Apparatus Ltd., Edenbridge, UK). Anaesthesia levels were assessed by examination of the cortical electroencephalogram (EEG; see below), and by testing reflexes to a cutaneous pinch or gentle corneal stimulation. Electrocardiographic (ECG) activity and respiration rate were also monitored constantly to ensure the animals' well being (see below). Mineral oil or saline solution (0.9% w/v NaCl) was applied to all areas of exposed cortex to prevent dehydration.

Parallel bipolar stimulating electrodes (constructed from nylon-coated stainless steel wires; California Fine Wire, Grover City, Calif., USA), with tip diameters of ~100 µm, a tip separation of ~150 µm, and an impedance of ~10 kΩ, were implanted into the right frontal cortex and right temporal cortex, and then affixed to the skull with dental acrylic cement (Associated Dental Products Ltd., Swindon, UK). The coordinates of the frontal stimulation site (AP: −4.2 mm, ML: −3.5 mm [bregma reference], and a depth of 2.3 mm below the dura[59]) correspond to the border region between the lateral and medial agranular fields of the somatic sensorimotor cortex[19, 20]. The coordinates of the temporal stimulation site (AP: +5.2 mm, ML: −6.9 mm, and a depth of 2.3 mm below the dura) approximately correspond to the primary auditory cortex[35].

The EEG was recorded via a 1 mm diameter steel screw juxtaposed to the dura mater above the right frontal cortex (AP: −4.5 mm, ML: −2.0 mm, which corresponds to the medial agranular field of the somatic sensorimotor cortex[19]) and referenced against an indifferent electrode placed adjacent to the temporal musculature. Raw EEG was band-pass filtered (0.1-2000 Hz, −3 dB limits) and amplified (2000×, NL104 preamplifier; Digitimer Ltd., Welwyn Garden City, UK) before acquisition. The ECG was differentially recorded via two silver wires that were inserted subcutaneously into the ipsilateral forelimb and hindlimb. Raw ECG was band-pass filtered (10-100 Hz) and amplified (5000×, NL104; Digitimer) before acquisition. The chest movements accompanying respiration were recorded using a miniature accelerometer (AP19, Bay Systems Ltd., Somerset, UK) and charge amplifier (Type 5007; Kistler Instrumente AG, Winterthur, Switzerland). The signal from the accelerometer allowed the depth and rate of respiration to be accurately assessed on- and off-line.

Extracellular recordings of LFPs and action potentials in the ipsilateral STN were simultaneously made with glass electrodes (6-12 MΩ in situ, tip diameters of 2.0-3.0 µm) that were filled with a 0.5 M NaCl solution containing 1.5% w/v Neurobiotin™ (Vector Labs, Peterborough, UK). Electrodes were lowered into the brain using a computer-controlled stepper motor (Burleigh IW-711; Scientifica Ltd., Harpenden, UK), which allowed the electrode depth to be determined with a resolution of 0.5 µm. Extracellular signals from the electrode were amplified (10×) through the active bridge circuits of two Axoprobe-1A amplifiers (Axon Instruments, Foster City, Calif., USA), bifurcated, and then differentially filtered to extract LFPs and unit activity. The LFPs were recorded after further amplification (100×; NL-106 AC-DC Amp, Digitimer) and low-pass filtering (between d.c. and 2 kHz; NL125 filters, Digitimer). Single units were recorded following AC-coupling, further amplification (100×; NL-106, Digitimer), and band-pass filtering (between 0.4 and 4 kHz; NL125, Digitimer). A HumBug™ unit (Quest Scientific, Vancouver, Canada) was used in place of a traditional 'notch' filter to eliminate mains noise at 50 Hz[12]. Action potentials were typically between 0.4 and 1.2 mV in amplitude and always exhibited an initial positive deflection.

The responses of the STN to cortical stimulation were determined by focal electrical stimulation of the cortex[48, 35]. Electrical stimuli, which consisted of single square-wave current pulses of 0.3 ms duration and variable amplitude (75-600 µA), were delivered to the ipsilateral frontal or temporal cortices at a frequency of 0.67 Hz using a constant current isolator (A360D; World Precision Instruments Ltd., Stevenage, UK) that was gated by a programmable pulse generator (Master-8: A.M.P.I., Jerusalem, Israel). The final recording location of each experiment was marked by discrete, extracellular deposits of Neurobiotin™ (100 nA anodal current; 1 s [50%] duty cycle for 60 min[46]). Following a period of 1-2 hr for the uptake and transport of the Neurobiotin™ by neurons and glia at the recording sites, animals were given a lethal dose of ketamine anaesthetic and perfused via the ascending aorta with 100 ml of 0.01 M phosphate-buffered saline at pH 7.4, followed by 300 ml of 4% paraformaldehyde and 0.1% glutaraldehyde in 0.1 M phosphate buffer, pH 7.4, and then by 150 ml of the same solution without glutaraldehyde. Brains were then post-fixed in the latter solution at 4° C. for at least 12 hr before sectioning.

Histochemistry

Standard techniques were used to visualize the Neurobiotin™ deposits[31a, 46]. Briefly, the fixed brain was cut into 60

μm thick sections in the coronal plane on a vibrating blade microtome (VT1000S: Leica Microsystems, Milton Keynes, UK). Sections were washed in PBS and incubated overnight in avidin-biotin peroxidase complex (1:100; Vector) in phosphate-buffered saline containing 0.2% Triton X-100 and 1% bovine serum albumin (Sigma). After washing, the sections were incubated in hydrogen peroxide (0.002% w/v; Sigma) and diaminobenzidine tetrahydrochloride (0.025% w/v; Sigma) in the presence of nickel ammonium sulphate (0.5% w/v; Sigma) dissolved in Tris buffer (0.05 M, pH 8.0) for 15-30 min. Neurobiotin™-filled cells were intensely labelled with an insoluble, black/blue precipitate. Finally, sections were dehydrated, cleared and mounted for light microscopy using standard techniques[8]. All final recording sites and the locations of the stimulation electrodes were histologically verified.

Data Acquisition and Analysis

Evoked LFPs and unit activity were sampled at 5 kHz and 10 kHz, respectively. The EEG signal was sampled at 5 kHz. The ECG and respiration signals were each sampled at 400 Hz. All biopotentials were digitized on-line with a PC running Spike 2™ acquisition and analysis software (version 4; Cambridge Electronic Design Ltd., Cambridge, UK). Evoked LFPs and EEG were high-pass filtered at 0.25 Hz off-line to remove slow 'DC drift' (Spike 2). Data from the recording session were first scrutinized for ECG-related artefacts; LFP data contaminated with such artefacts were rejected. Because some data sets did not follow a normal distribution (One-sample Kolmogorov-Smirnov Test for 'normality'), statistical comparisons of unpaired data were performed using the Mann-Whitney U test. The criterion for significance was the 95% level (unless stated otherwise). Data are expressed as mean±standard deviation (SD).

Peristimulus time histograms (PSTHs) were constructed from 200 consecutive stimulation trials, with a bin size of 1 ms[35]. The cumulative sum (CUSUM) technique, a sensitive method for quantitatively assessing trends in PSTH profiles with respect to a pre-stimulus control, was used to statistically define the responses of units to cortical stimulation[24]. The criteria used to establish significant excitatory or inhibitory responses were changes in CUSUM above or below, respectively, thresholds set at the mean CUSUM score during the 95 ms immediately preceding stimulation±2 SDs of this mean. Response latencies were calculated according to the first bin in which a response reached significance. The 'peak' of an excitation response was defined as the bin with the highest spike count. The 'peak' of an inhibition response was defined as the bin with the lowest spike count or, in the case of a cessation in firing, the bin in the middle of the statistically-significant inhibition. Peristimulus averages of the evoked LFPs were generated from the same 200 stimulation trials used for the PSTHs. Positive or negative deflections in the average evoked LFP were considered significant if the peaks and troughs of such deflections exceeded threshold voltages defined as ±2 standard errors of the pre-stimulus mean.

Results

Unit Activity Evoked by Cortical Stimulation

Figure 2:
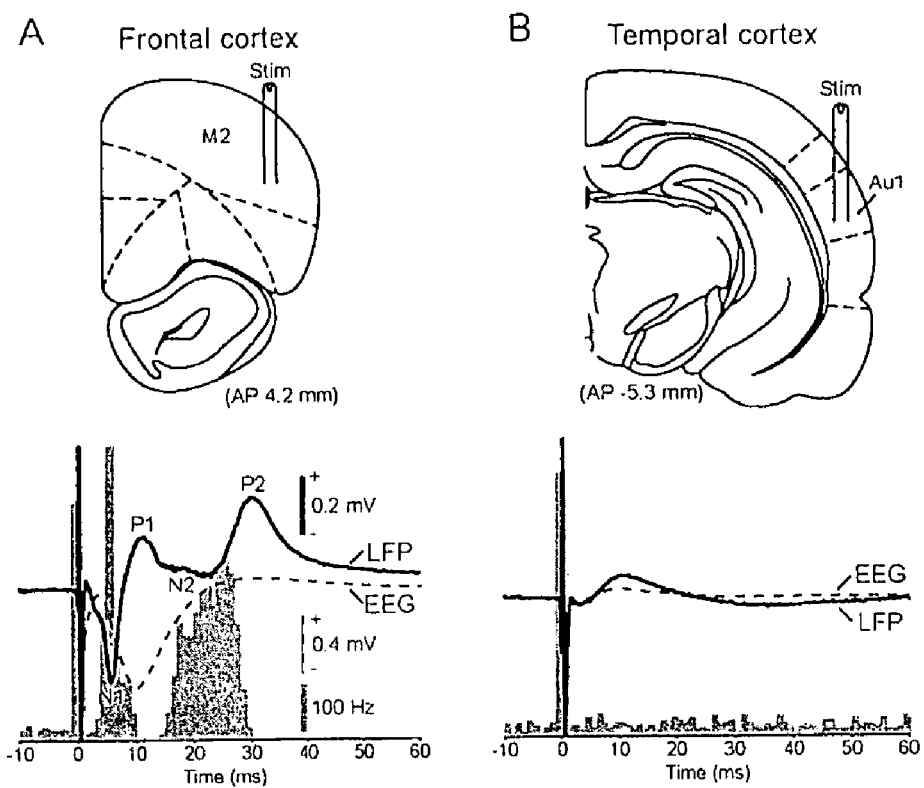
FIG. 2. Evoked unit activity in the subthalamic nucleus is tightly correlated with local field potentials and is organised according to cortical region. (Top) Schematic representations of the positions of the stimulating electrodes (Stim) in the frontal (A) and temporal (B) cortices. (A) Stimulation of the frontal cortex at 300 µA evoked a characteristic unit response that was consistently mirrored by contemporaneous deflections in the local field potential (LFP; solid line shows peristimulus average of LFP) recorded from the same electrode. Excitations at the single unit level were accompanied by negative deflections in the LFP (N1 and N2), whilst inhibitions were associated with positive deflections in the LFP (P1 and P2). The LFP in STN was dissimilar to the field potential evoked in the frontal cortex by the same stimuli (dashed line; EEG). (B) Stimulation of the temporal cortex (600 µA) did not evoke a response from the same neuron. Accordingly, field potentials in the STN and frontal cortex exhibited a different, smoother profile. In this and the following figures, positivity is signified as upward deflections of LFPs. Calibration bars in (A) also apply to (B). Stimulation artefacts were truncated for clarity. AP (anterior-posterior) numbers denote positions with respect to Bregma. M2, secondary motor cortex, Au1, primary auditory cortex.
Figure 3:
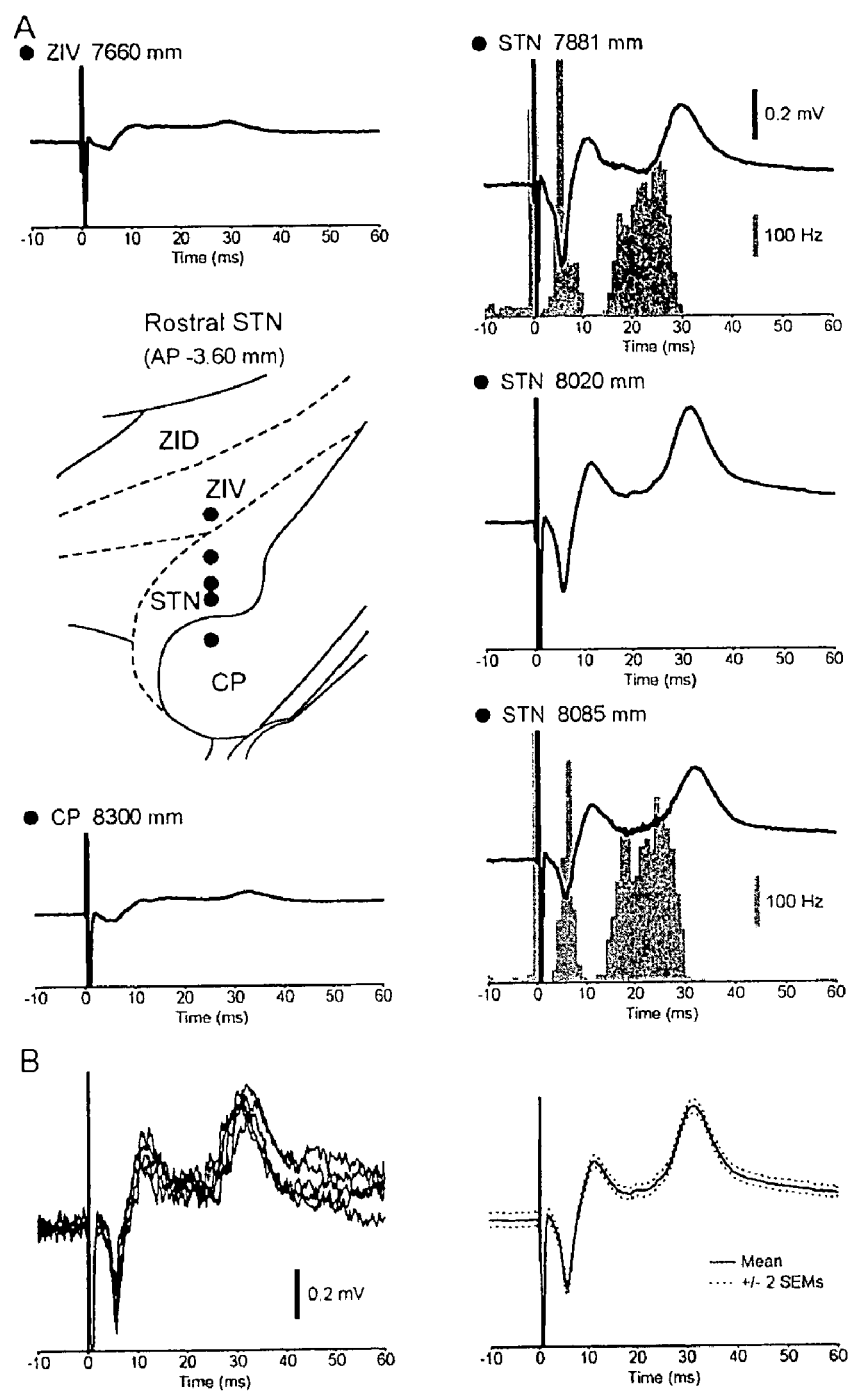
FIG. 3. Multiphasic unit responses and local field potentials evoked in the subthalamic nucleus by frontal cortical stimulation are stereotypical and are not expressed in neighbouring structures. (A) Schematic representation of recording sites in one vertical pass of the electrode through the brain at the level of the rostral half of the subthalamic nucleus (STN). Figures denote depths of recording sites from the cortical surface. Stereotypical, multiphasic unit and local field potential (LFP) responses were observed throughout the dorsoventral axis of the STN. Neurons located within a few hundred microns of each other shared similar response profiles (STN neurons at depths of 7881 μm and 8085 μm). Multiphasic LFPs could still be recorded in the STN in the absence of unit activity (recording site at 8020 μm). Vigorous LFP responses of the type seen in STN were not observed in the ventral division of the zona incerta (ZIV) nor the cerebral peduncle (CP); the small LFP deflections in the two cases shown were not significant. (B) Stereotypical LFPs in STN were robust and repeatable. Five superimposed LFP traces, each evoked sequentially by a single stimulus (left); peristimulus average of 200 evoked LFPs with standard errors (right). Calibration bar for LFP in STN (7881 μm) applies to all LFPs in (A). Calibration bar in the left panel of (B) applies to the right panel. Stimulation artefacts were truncated for clarity. AP (anterior-posterior) numbers denote positions with respect to Bregma. ZID, dorsal division of the zona incerta.
Figure 4:
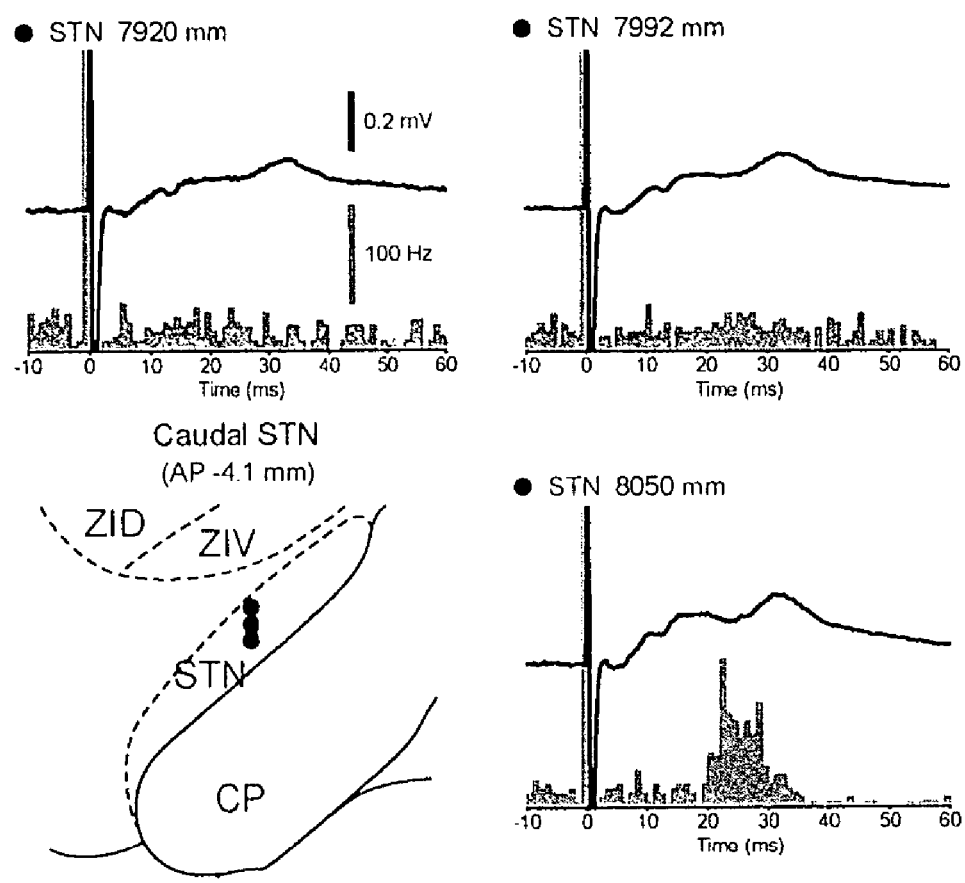
FIG. 4. Unit responses and local field potentials evoked in the subthalamic nucleus by frontal cortical stimulation are topographically organised. (Bottom left) Schematic representation of recording sites in one vertical pass of the electrode through the caudal half of the subthalamic nucleus (STN). Figures denote depths of recording sites from the cortical surface. Note that these neurons were recorded from the same animal as that shown in FIG. 3. (Top left and right) The multiphasic unit and local field potential (LFP) responses that were observed in rostral STN were not observed in caudal STN. Caudal STN neurons did not usually respond to frontal cortical stimulation (STN neurons at depths of 7920 μm and 7992 μm) and robust LFP responses of the kind recorded in rostral STN were not observed. Neurons located within a few hundred microns of each other generally shared similar 'response' profiles (neurons at 7920 82 m and 7992 82 m). However, two cells did respond with a long-latency excitation and a weak, long-latency, long-duration inhibition, which were reflected in the LFP (e.g. the neuron at 8050 82 m). Note the absence of short-latency responses was correlated at the level of the LFP by a lack of distinct N1 and P1 deflections. Calibration bars for units and LFP in STN (7920 82 m) apply throughout. Stimulation artefacts were truncated for clarity. CP; cerebral peduncle, ZID, dorsal division of the zona incerta; ZIV, ventral division of the zona incerta.
Figure 8:
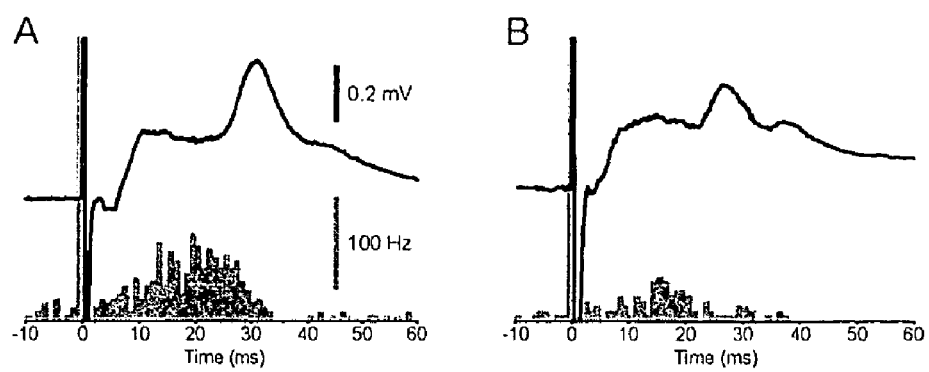
FIG. 8. Atypical unit responses and local field potentials evoked in the subthalamic nucleus by cortical stimulation. (A, B) A small number of rostral neurons did not exhibit short-latency excitation or short-latency inhibition responses to stimulation (at 300-600 82 A), but did exhibit long-latency excitations and inhibitions. The local field potentials (LFPs) evoked in these cases were also unusual, but still reflected unit activity; short-latency N1 and P1 deflections were small or absent from the corresponding LFPs, but the N2 and P2 deflections were still present. Calibration bars in (A) apply to (B). Stimulation artefacts were truncated for clarity.

The responses of a total of 69 neurons to stimulation of the ipsilateral frontal cortex were recorded throughout STN. The spontaneous activities of these STN neurons were similar to those previously described[45, 46], i.e. mean firing rates of ~10 Hz, with tonic, irregular firing or periodic, bursting patterns. The majority of the STN neurons (61%) responded to frontal cortical stimulation at an intensity of 300 μA (or 600 μA; see below) in a typical, 'multiphasic' fashion (FIGS. 1 and 2). These neurons responded with, in turn, a short-latency brief excitation, a short-latency brief inhibition (27 of 42 responsive neurons) or a marked reduction in firing (15 neurons), a long-latency excitation and finally a long-latency, long-duration inhibition (FIGS. 1A and B). The mean latencies of these ordered responses were 4.5±1.6 ms, 10.4±3.0 ms, 16.6±4.7 ms and 30.6±5.5 ms, respectively. All neurons that responded in this characteristic manner were located in the rostral half of STN (FIG. 3). The responses of a small minority of STN neurons (n=8) were more variable; only some of the phases of the typical, multiphasic unit response were expressed e.g. no short-latency excitation (FIG. 1C), a short-latency excitation only (FIG. 1D), or a long-latency excitation and/or long-latency inhibition only (FIGS. 4 and 8). Most of the STN neurons that did not respond to cortical stimulation (300 or 600 μA; 15 of 19 neurons) were located in the caudal half of the nucleus (FIG. 4). These data suggest that, in agreement with previous studies[35], the responses of single STN neurons are complex and topographically organised.

The stereotyped response of single neurons in the rostral half of STN to each cortical stimulus (exemplified by the structured form of individual PSTHs), together with the fact that the responses of neurons at different recording sites within rostral STN were alike (exemplified by the similarities between the PSTHs of different neurons), raises the possibility that unitary responses may be synchronised by each cortical stimulus. To characterise better the degree of synchrony imposed upon STN neurons by cortical input, 9 pairs of neurons were recorded with single electrodes during stimulation. In every case, the responses of both neurons in the pair were qualitatively and quantitatively similar. Seven of the nine pairs responded to cortical stimulation in the typical multiphasic manner (FIG. 1E). The remaining two pairs of neurons were located in caudal STN and did not respond to cortical stimulation (data not shown).

The fact that the responses of neighbouring neurons were similar suggests that descending cortical input can have a synchronising influence on the STN and the circuits involved in STN responses. To test the hypothesis that larger, more spatially-distributed populations of STN neurons are synchronised in a similar manner by cortical stimulation, we recorded LFPs evoked simultaneously with the responses of units. Because LFPs are the result of the synchronised, sub-threshold and suprathreshold activities of local neural populations, they may be good indicators of synchronisation in the STN[30, 53].

Correlations Between Evoked Unit Responses and Local Field Potentials

Local field potentials evoked in rostral STN by frontal cortical stimulation consistently mirrored the simultaneously-recorded single unit responses (FIGS. 2A and 3A). A brief negative deflection in the LFP ('N1'; mean latency to the 'peak' of the deflection of 5.4±1.3 ms; n=42) occurred in time with the short-latency excitation seen in the unit response. A brief positive deflection in the LFP ('P1'; mean latency to the peak of the deflection of 11.9±2.8 ms) occurred at the time of the short-latency inhibition or the reduction in firing. A second negative deflection ('N2'; mean latency to peak of 21.6±3.9 ms) was closely associated with the long-latency excitation response. The mean latencies of the peaks of the N1, P1 and N2 deflections were not statistically different from the mean latencies of the 'peak' of each of the corresponding phases of the unit response (the mean peaks of the short-latency excitation, short-latency inhibition and long-latency excitation responses occurred at 6.0±2.0 ms, 12.8±3.5 ms and 22.7±3.9 ms, respectively). The final LFP deflection, a second positive deflection ('P2'; mean peak latency of 30.1±3.1 ms), coincided with the start of the long-latency, long-duration inhibition (FIGS. 2A and 3A).

Dependence of Evoked Responses on Cortical Connectivity

Figure 6:
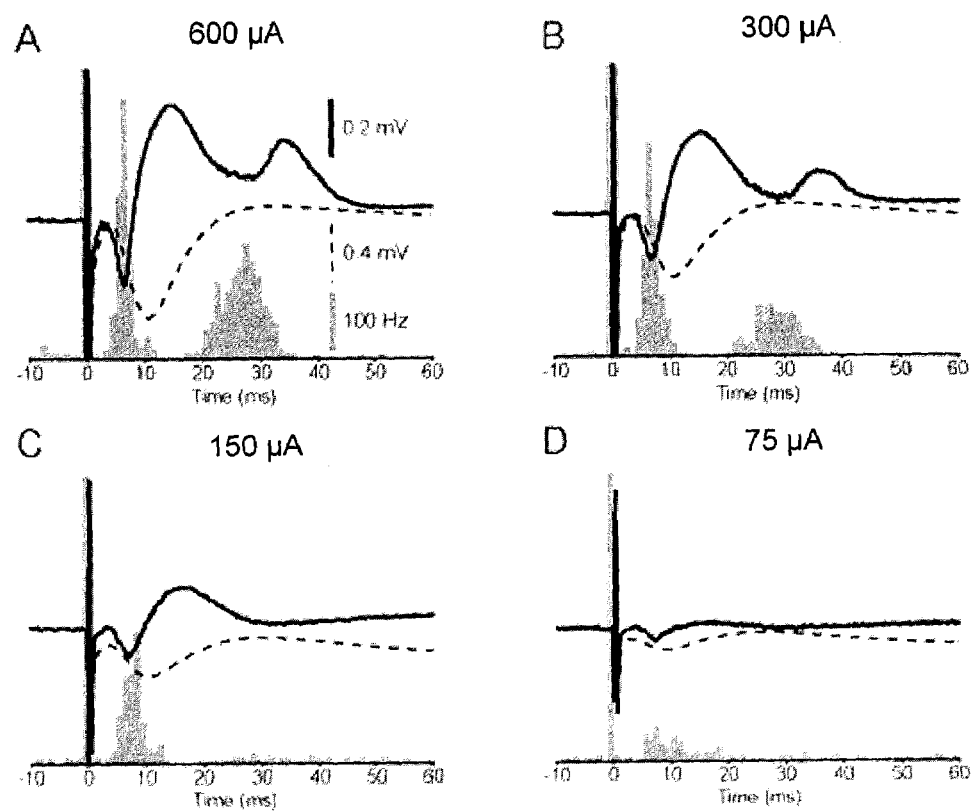
FIG. 6. Unit responses and local field potentials evoked in the subthalamic nucleus co-vary with stimulus intensity. (A) Typical responses of a rostral unit, the local field potential (LFP) and the cortical EEG (dashed line) to frontal cortical stimulation at an intensity of 600 82 A. (B) Reducing the stimulus intensity to 300 82 A did not alter the qualitative nature of the responses, although there were small, but commensurate, changes in the absolute magnitudes of the responses. (C) A further reduction in current intensity to 150 82 A resulted in an attenuation of the short-latency excitation and inhibition responses and a failure of the long-latency responses. Changes in the evoked LFP were commensurate with these alterations in the unit response; the amplitudes of the N1 and P1 deflections were reduced, whilst the N2 and P2 responses virtually disappeared. (D) Only the weak, short-latency excitation, with a corresponding small, negative deflection in the LFP, remained at a stimulus intensity of 75 82 A. Same neuron recorded in (A-D). Calibration bars in (A) apply to all panels. Stimulation artefacts were truncated for clarity.

The LFPs evoked in STN were not closely related to field potentials that were simultaneously evoked in the frontal cortex itself, as measured in the EEG; suggesting that volume conduction of cortical activity was not responsible for the subthalamic LFP (FIGS. 2 and 6). Electrical stimulation of temporal cortex, which, unlike the frontal cortex, does not project directly to the STN[14, 35], failed to elicit stereotypical, multiphasic unit and LFP responses in any of the STN regions examined (14 neurons tested; FIG. 2B). If widespread excitation of cortical neuronal structures by excessive current flow was occurring, then one would expect similar responses in STN when stimulating either of these distant and functionally-distinct cortical regions. Thus, the relatively low-intensity electrical stimuli used in this study probably activated only a small, circumscribed area of cortex, further implying that unit and LFP responses were dependent on cortical connectivity and not volume conduction effects of cortical stimulation per se.

Although these stereotypical, multiphasic LFPs were tightly correlated to unit responses, they were unlikely to be the result of suprathreshold activity in the soma and dendrites of just one or a few neurons in close proximity to the tip of the recording electrode because the LFPs could be recorded easily when unit activity could not (FIG. 3A). Moreover, the evoked LFPs were robust and repeatable, such that N1, P1, N2 and P2 deflections could be clearly discerned without averaging i.e. 'on-line' in response to a single stimulus (FIG. 3B).

Topographical Organisation of Evoked Responses within the Subthalamic Nucleus

Unit response failures to frontal cortical stimulation, which most commonly occurred in the caudal half of STN, were not accompanied by the stereotypical evoked LFP (n=16; FIG. 4), further indicating that these LFPs were topographically organized and that the stimulation current was not excessive. Although neurons in the caudal half of STN did not demonstrate the multiphasic response typical of cells in rostral STN, two neurons did respond with a long-latency excitation and a weak, long-latency long-duration inhibition (FIG. 4). The absence of short-latency responses was correlated at the level of the LFP by a lack of distinct N1 and P1 deflections. Moreover, the long-latency unit responses were associated with small N2 and P2 deflections (also see FIG. 8).

Spatial Specificity of Evoked Responses

Figure 5:
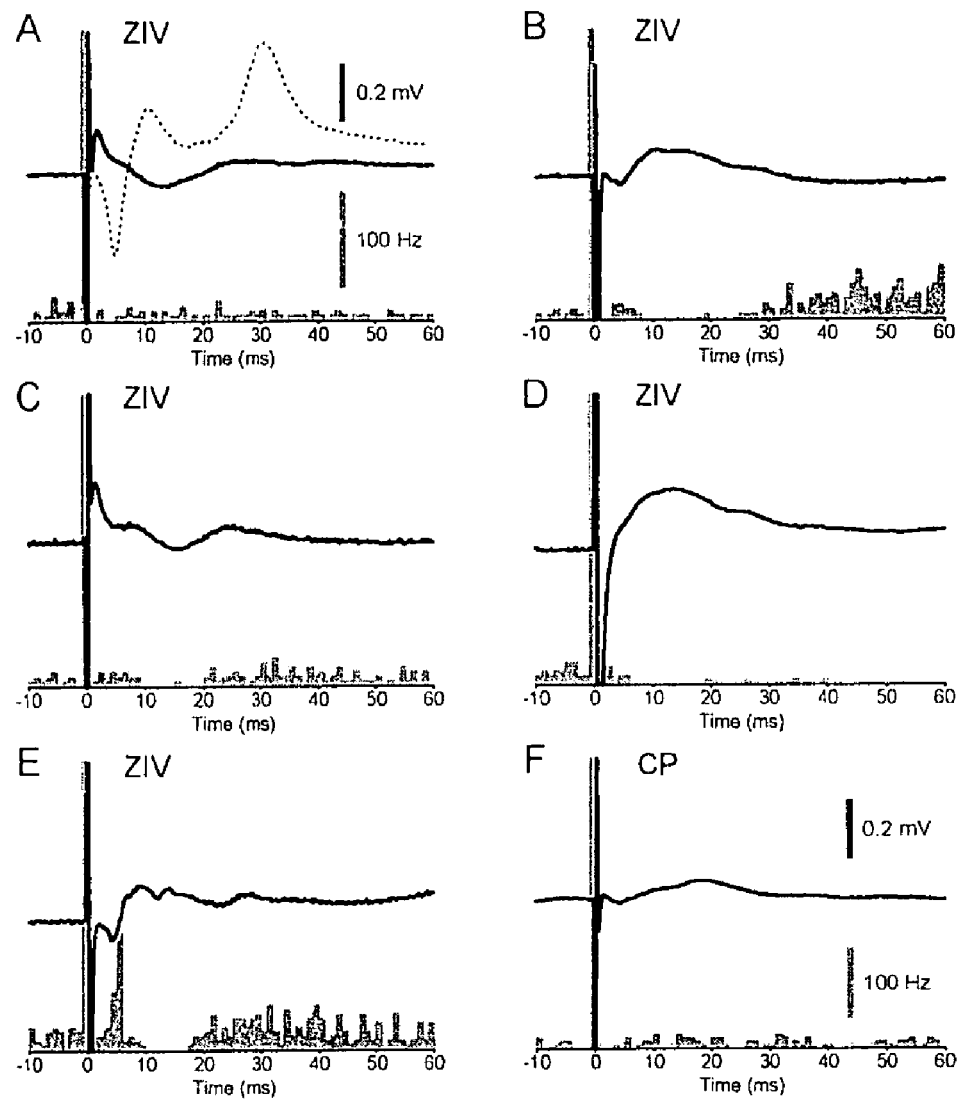
FIG. 5. Unit responses and local field potentials evoked in the zona incerta and cerebral peduncle are variable and are not strongly correlated. (A) Most neurons in the ventral division of the zona incerta (ZIV) did not respond to cortical stimulation (300-600 82 A). Evoked LFPs recorded with non-responsive ZIV neurons were of small amplitude and were unpredictable. Dotted line shows multiphasic LFP evoked in rostral STN for comparison. (B-E) In contrast to the subthalamic nucleus, the discharges of the responsive ZIV neurons were variable and were usually not clearly correlated with the evoked LFPs. (F) The small number of neurons recorded in the cerebral peduncle (CP) did not respond to cortical stimulation, and LFPs evoked in the peduncle were relatively smooth and featureless. Calibration bars in (A) apply to (B-E). Stimulation artefacts were truncated for clarity.

To test whether the multiphasic evoked LFP was confined to STN, unit and LFP responses were also recorded from neighbouring brain regions. The LFP typically evoked in rostral STN was not observed in surrounding structures, such as the zona incerta, the cerebral peduncle and the internal capsule (FIGS. 3A and 5), supporting the idea that the LFP is due to the synchronous activity of many neighbouring STN neurons and is not strongly influenced by activity in surrounding (proximal) structures. Most neurons in the ventral division of the zona incerta (ZIV) did not respond to cortical stimulation (13 of 20 neurons tested; FIG. 5A). Evoked LFPs recorded with non-responsive ZIV neurons were of small amplitude and were unpredictable (FIGS. 3A and 5A). The discharges of the responsive ZIV neurons were highly variable and were not clearly correlated with the wide variety of LFPs that were evoked in this region (FIG. 5B-E). Neither the unit activity nor LFP bore a strong relationship to the responses in STN. Neurons in the cerebral peduncle (CP) were only rarely observed (n=3). None of the CP neurons responded to cortical stimulation and evoked LFPs were relatively smooth and featureless (FIGS. 3A and 5F).

Relationship of Evoked Responses to Stimulus Intensity

To ensure that stimulation at a current intensity of 300 µA was effectively maximal, and to test the possibility that different phases of the characteristic unit and LFP responses were differentially sensitive to input intensity, current-response relationships were studied. The profile of the LFP and the unit responses evoked in STN by frontal cortical stimulation were both dependent on the intensity of the current that was delivered (FIG. 6). There were no qualitative differences in the response profiles evoked by stimulation at 600 µA and 300 µA (FIGS. 6A and B), and although the absolute magnitudes of the phasic responses varied slightly, no significant differences in latencies were observed (n=9 neurons). Thus, the responses to stimulation at 300 µA were maximal with respect to the pattern of the response. However, reducing the current intensity to 150 µA or 75 µA resulted in distinct and corresponding changes in the unit and LFP responses (FIGS. 6C and D). The short-latency responses were attenuated, as were the associated LFP deflections (N1 and P1), and the longer-latency unit responses tended to fail together with the related LFP deflections (N2 and P2). The short-latency excitation and N1 responses were the last to fail at the lowest current intensity (FIG. 6D).

Relationship of Evoked Responses to Brain State

Figure 7:
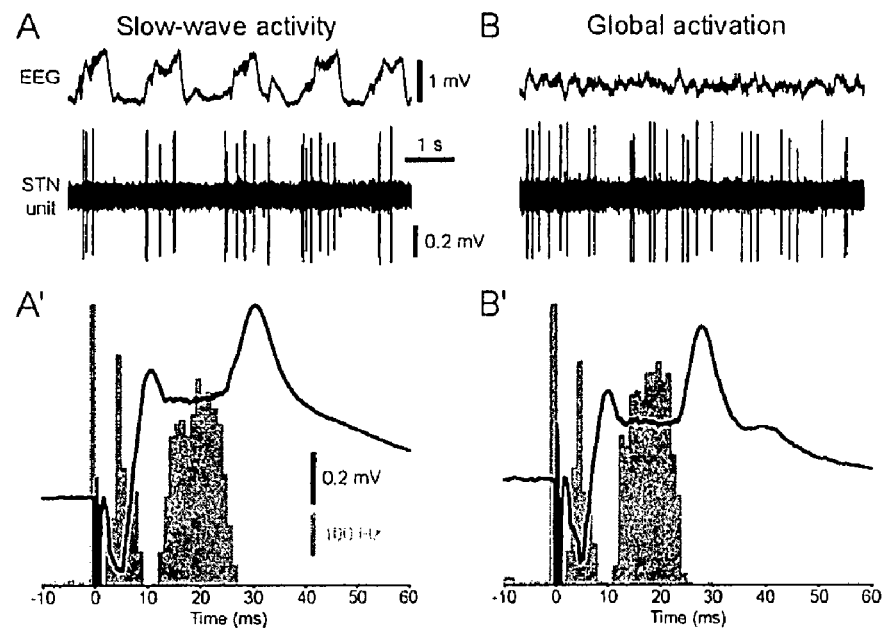
FIG. 7. Unit responses and local field potentials evoked in the subthalamic nucleus by cortical stimulation are not strongly dependent on brain state. (A) During slow-wave activity, cortical activity (EEG) was dominated by a large-amplitude, slow oscillation. Unit activity in STN was closely related to the slow-wave activity present in the cortex; STN neurons commonly exhibited low-frequency oscillations in firing. (A') Unit and local field potential (LFP) responses evoked during slow-wave activity (a few seconds after recording shown in A) were robust and were of stereotypical, multiphasic natures. (B) Global activation was characterised by a prolonged loss of the large-amplitude, slow oscillation in the cortex and was associated with a change in the activity of the STN neuron to irregular, tonic firing at a higher rate. (B') The multiphasic responses of the same STN neuron and associated LFP as evoked during global activation (a few seconds after recording in B) did not substantially differ in pattern from responses evoked during slow-wave activity. Calibration bars in (A) apply to (B), bars in (A') apply to (B'). Stimulation artefacts were truncated for clarity.

The urethane-anaesthetised rat is a good model for determining the impact of extremes of forebrain activity on the BG[46]. Activity in the cortex spontaneously shifts from 'slow-wave activity' (FIG. 7A), which is similar to activity observed during natural sleep, to a state of 'global activation' (FIG. 7B), which contains patterns of activity that are more analogous to those observed during the awake state, and vice versa[69]. To test whether alterations in ongoing forebrain activity could affect the profiles of the evoked responses in STN, we recorded and compared responses evoked during both slow-wave activity and global activation. Spontaneous shifts in the global brain state of the animal, as assessed from the cortical EEG, did not greatly affect the multiphasic responses to cortical stimulation (6 neurons; FIGS. 7A' and B'). There were no qualitative differences in the patterns of the unit responses or LFPs evoked by stimulation during the two brain states and although the absolute amplitudes of the multiphasic responses varied slightly, no significant differences in latencies were observed.

Atypical Evoked Responses

The unusual nature of the responses of a small population of neurons was often reflected at the level of the evoked LFP. When STN neurons (n=4) did not exhibit short-latency excitation or short-latency inhibition responses, then short-latency N1 and P1 deflections were small or absent from the LFP (FIGS. 8A and B); longer-latency unit responses were still associated with N2 and P2 deflections (FIGS. 8A and B).

Discussion

Taken together, these results demonstrate that both direct and indirect cortical activity has a powerful synchronising effect on discrete ensembles of STN neurons. Synchronised unit activity in STN is consistently reflected at the population level as multiphasic LFPs, which are organised according to the topography and intensity of cortical input. As such, LFPs evoked in STN are good indicators of the functional connectivity of the underlying neuronal population.

Circuit Interactions Underlying Evoked Unit Responses in the Subthalamic Nucleus The STN receives monosynaptic inputs from select areas of the ipsilateral cerebral cortex, including prefrontal, premotor, primary motor, cingulate and, to a lesser extent, somatosensory cortex[67]. The first response of most neurons in the rostral half of STN to stimulation of the ipsilateral frontal cortex was a brief, but powerful, excitation with a mean latency of 4.5 ms. This short-latency excitation has been described by many others and is almost certainly driven by the direct, excitatory corticosubthalamic projection[33, 62, 63, 64, 25, 6, 48, 56, 35]. The multiphasic nature of the typical unit response develops from disynaptic and polysynaptic interactions, which are slower to manifest. The second phase of the unit response, a brief, short-latency (mean 10.4 ms) inhibition, probably arises from feed-forward excitation of GP neurons by inputs from STN, and then feed-back inhibition of STN neurons by the reciprocally-connected neurons of the GP[32, 63, 64, 25, 48, 56]. A disinhibition of STN neurons, mediated by feed-forward connections through the NS and GP and then on to STN, has been proposed to account for the third phase of the response, a long-latency (mean 16.6 ms) excitation[48, 56]. Alternatively, it may be that this late excitation represents the latter parts of a prolonged response of STN neurons to short-lasting cortical input[64, 25].

The short-latency excitation responses of pairs of neighbouring STN neurons were similar and, when present, co-varied, which demonstrates that the connectivity of the corticosubthlamic projection is such that it can support the synchronous recruitment of neighbouring target neurons. Because short-latency inhibitions were also synchronised, it is also likely that the activity of neurons in GP, and subsequently in STN, was synchronised by the correlated discharges of STN neurons that were driven by corticosubthlamic input. Synchronous, long-latency excitations suggest that disfacilitatory processes were also widespread. These findings argue that, despite potentially complex circuit interactions, responses tend to be similar within small, local populations of neurons.

Unit responses were topographically organised within STN. A small minority of STN neurons, most of which were located in the caudal half of STN, did not respond to cortical stimulation. These findings are in good agreement with previous anatomical[2, 14, 35] and physiological[35] studies, which have shown that the frontal cortical areas stimulated in the present study project throughout most of the dorsoventral axis of the rostral two thirds of STN only. The caudal one third of STN receives input from the caudal aspects of the medial frontal cortex[2], which was presumably not activated by the electrical stimulus used in this study. The present data are also in keeping with studies demonstrating that the (auditory) temporal cortex does not project directly to STN[14, 35]. Response differences were unlikely to be due to insufficient current flow at the site of stimulation because responses were maximal with respect to pattern at the stimulus intensities used. Similarly, the unresponsive nature of these neurons was probably not a function of anaesthetic depth because the pattern of responses did not dramatically alter across brain states. The fact that unit and LFP responses to corticosubthalamic input were topographically organised and thus, did not conflict with the known anatomy, adds further functional significance to these stimulation data and imply that the currents used were not excessive.

Upon reduction of the stimulus intensity, polysynaptic responses failed before the monosynaptic response, suggesting that the indirect, trans-striatal and trans-pallidal pathways to output nuclei may be represented at the population level in STN according to the intensity of descending cortical activity. These findings further demonstrate that the corticosubthalamic pathway is likely to have a proportionally greater influence on STN activity than these other pathways at any given input intensity. This, together with the fact that the corticosubthalamic projection is the swiftest route by which the relevant areas of cortex can influence activity in the output nuclei of the BG[49, 56], argues in favour of the STN as a critical input station of the BG[51, 57, 9].

Neural Basis of Local Field Potentials Evoked in the Subthalamic Nucleus

The recording of LFPs evoked together with unit responses allowed us to test the hypothesis that the responses of larger, more spatially-distributed populations of STN neurons were also synchronised to the high degree exhibited by pairs of neighbouring cells. The STN in rodents and primates is a compact, unlayered structure, comprising an homogeneous population of glutamatergic projection neurons with complex and varied dendritic fields[75, 31, 1, 67]. Fibres of passage and afferent axons in STN do not conform to any strict or laminated arrangement[1]. Intrinsic organisations such as this can make the interpretation of current flows, and hence extracellular potentials, challenging[30]. Despite this, several temporal and spatial correlations between evoked LFPs and unit activity were reliably observed.

Figure 9:
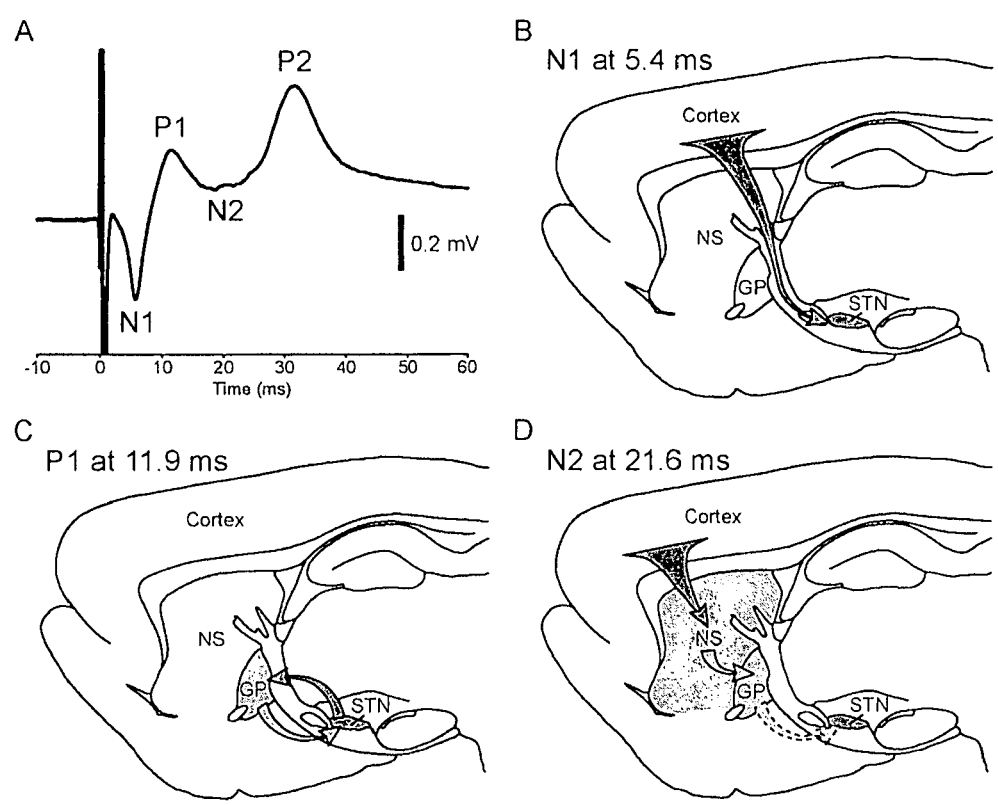
FIG. 9. Neuronal circuits underlying the cortical stimulation-evoked local field potential in subthalamic nucleus. (A) The stereotypical, multiphasic profile of the local field potential (LFP) evoked in subthalamic nucleus (STN). The LFP was likely a consequence of activity in monosynaptic and polysynaptic circuits. (B-D) Times are mean latencies to peak deflections. Shaded basal ganglia nuclei contribute to that particular phase of the response in STN; white nuclei do not contribute. Dark grey arrows represent excitatory pathways. Light grey arrows represent inhibitory pathways. (B) The short-latency, negative deflection, N1, was probably due to activation of the direct corticosubthalamic pathway. (C) The short-latency, positive deflection, P1, probably arose as a consequence of feed-forward excitation of globus pallidus (GP) by STN and then feed-back inhibition of STN by GP. (D) The long-latency, negative deflection, N2, was most likely due to disinhibition of STN through inhibition of GP by neostriatum (NS) in a feed-forward manner. Arrow with dashed line represents disinhibition. The circuits that may underlie the long-latency (mean 30.1 ms), positive deflection, P2, are unknown.

The first response of most STN neurons to cortical stimulation, i.e. the short-latency excitation, coincided with a prominent negative deflection (N1) in the LFP (FIG. 9A). Theoretical and experimental studies suggest that LFPs are a consequence of current flow related to synchronised, post-synaptic potentials, rather than current flow across pre-synaptic and axonal membranes[30, 53]. We propose that the N1 deflection in the LFP was the result of concerted subthreshold and suprathreshold population activity in STN that was driven by monosynaptic cortical input (FIGS. 9A and B). In agreement with this, the activity of neighbouring STN neurons was synchronously increased by the stimulus[65] and, when single units did not respond with a short-latency excitation, the N1 deflection was much smaller or absent. The second phase of the unit response to cortical stimulation, a brief reduction in activity, which was likely caused by feed-back inhibition from GP neurons[7], was associated with a brief, positive deflection (P1) in the LFP (FIG. 9A). This positive deflection likely reflected the synchronous hyperpolarisation of STN neurons by pallidal inputs (FIGS. 9A and C). Support for this comes from intracellular recordings[33, 25] and the fact that when single units did not respond with a short-latency inhibition, the P1 deflection was not distinct. The subsequent long-latency excitation, presumably due to the disinhibition of STN neurons and/or the continued excitation of STN neurons by cortical input (see above), was accompanied by a second negative deflection (N2) in the LFP (FIGS. 9A and D). The cellular and synaptic mechanisms underlying the final phase of the unit response, a long-duration inhibition, are unknown, although 'cortical disfacilitation' has been hypothesised to be the cause[25]. The start of this phase again was associated with a positive deflection (P2) in the LFP (FIG. 9A), a finding corroborated by previous intra-cellular data indicating that the long-duration inhibition is due to membrane hyperpolarisation[33]. These precise temporal correlations between unit and population responses suggest that synchronous cortical inputs can impose widespread synchronisation within STN and associated feed-back and feed-forward neuronal circuits.

In agreement with the topographic organisation of unit responses, spatial correlations between units and LFPs were also consistently observed in addition to temporal correlations. Neurons in the caudal half of STN did not respond in the multiphasic way that was typical of neurons in rostral STN. In these cases, the characteristic evoked LFP was either very small, or, more commonly, not seen at all. These observations substantiate the idea that the LFPs were the result of the synchronous activity of ensembles of functionally-related STN neurons and argue against a significant contribution to LFPs from volume-conducted activity. The stereotypical unit responses and LFPs observed in STN were not found in the zona incerta or cerebral peduncle. Furthermore, in zona incerta, unit responses were not clearly related to LFPs, despite the fact that this area also receives monosynaptic inputs from frontal cortical areas[52]. This implies that the synchronisation of unitary responses in STN is not simply the result of the synchronised corticofugal volleys induced by stimulation, but must also entail some fundamental differences in the organisation of direct cortical inputs to neighbouring neurons in STN as compared to neurons in ZIV and/or the intrinsic composition of these nuclei. The unit and population responses recorded in zona incerta and the cerebral peduncle also act as useful controls for the data from STN recordings that support the idea that the multiphasic LFP in STN is the result of the synchronised activity of a local population of neurons and, as such, is characteristic of STN.

The high predictability and specificity of the evoked LFPs, together with their topographic nature, have three important implications. First, these data suggest that the geometry of the major dipoles dictating current flow in STN, i.e. the somata and dendrites of neurons, may be more ordered than previously thought. Secondly, the correlations we have observed between units and evoked LFPs may help in the interpretation of LFPs commonly observed in STN in other paradigms[13], particularly high-frequency LFP oscillations since rapid sequences of excitations and inhibitions at the unit level are reflected in the LFP with good time resolution. Thirdly, the evoked LFP data provide a framework for studying interactions between the cortex and basal ganglia at the population level and for elucidating mechanisms that may not be readily apparent at the level of single units.

Functional Implications

Applied to the cerebral cortex, electrical stimuli send a highly synchronised volley of impulses through bundles of descending corticofugal axon fibres. This evoked direct and indirect input to STN had a profound synchronising effect on select populations of STN neurons. The same stimuli did not have the same effect on the zona incerta, despite the fact that it also receives direct inputs from frontal and/or prefrontal cortices[52]. This implies that the STN is intrinsically organised to react in this correlated manner to synchronised cortical input. The important question that arises is whether the STN in normal or pathological conditions receives synchronised inputs. Neurons in cortical areas projecting to STN exhibit a wide range of synchronous network activity during natural behaviours[54, 55, 36, 21, 4]. In particular, synchronised oscillations, which are caused by periodic, phase-locked discharges of cortical cell assemblies, are frequently observed in cortex during sensory-motor integration and other complex behaviours that probably involve the basal ganglia[61, 44, 22, 23]. Thus, corticosubthalmic input may be highly synchronised under certain conditions, which might, in turn, promote synchronous activity in STN. The present stimulation data suggest that discrete populations of STN neurons will be driven to fire in a highly ordered and correlated fashion by synchronised cortical input. Consistent with this, emergent cortical oscillations have been shown to synchronise unit activity in STN[45, 46, 72, 3]. Furthermore, the STN may express synchronous oscillations, as evinced in unit or LFP recordings, under both normal and pathological conditions[10, 12, 39, 13]. Some oscillations in STN are related to movement and are dependent on dopamine, suggesting they are of functional significance[11, 12, 39, 73, 74]. Moreover, simultaneous recordings have shown that oscillatory population activity in STN may be significantly coherent with that in cortex, and that the time lags between oscillations are consistent with the synaptic delay along the direct corticosubthalamic projection[56, 47, 15, 73].

The present data highlight two additional considerations of importance. The response evoked in the cortex itself, as measured in the EEG, was entirely different to the evoked STN response, as recorded in the LFP, suggesting that BG circuits are able to generate activity over and above that expressed by the cortex. Secondly, the fact that the short-latency excitation response of STN neurons and associated LFP deflection (N1) were last to fail upon reduction of stimulus intensity suggests that STN neurons receiving monosynaptic cortical input are likely to respond most vigorously and reliably to that input when activated, compared to subsequent inputs derived from polysynaptic circuit interactions. Taken together, the current data add weight to the proposed importance of the corticosubthalamic projection[51, 57] and synchronous ensemble activity in information processing in corticobasal ganglia circuits[23].

The STN is an important target for surgical treatment of Parkinson's disease and perhaps, in the future, intractable epilepsy, partly because of the proven clinical benefits of 'deep brain stimulation', in which neuronal activity is modified by electrical stimulation through electrodes implanted in STN[38, 40 43, 16]. However, surgical implantation of electrodes is challenging because of the difficulties of unequivocally locating the STN and key neighbouring structures[68, 70]. The finding that LFPs evoked in STN by stimulation of the cerebral cortex are unique amongst surrounding structures indicates that evoked LFPs could act as electrophysiological 'fingerprints' that might greatly aid the identification of the STN and, perhaps more importantly, specific regions within or above STN[66, 70]. Electrophysiological recordings of STN activity are now routinely used in implantation surgery to refine the positioning of the stimulation electrode[68, 60] and because the evoked LFPs are relatively resistant to changes in brain state, patient anaesthesia may not be an issue. Furthermore, LFPs can be recorded in STN from micro-electrodes, or the macro-electrodes that are used for stimulation, without great difficulty[11, 18, 39, 41], and importantly, evoked LFPs could be evaluated after only a few cortical stimuli (i.e. within a few seconds intra-operatively). There is also some evidence to suggest that our approach could potentially be extrapolated for use with a non-invasive stimulation technique, such as transcranial magnetic stimulation, thereby increasing its potential clinical value[37].

Transcranial magnetic stimulation (TMS) is a recognised non-invasive technique currently used in the treatment of epilepsy in patients with implanted, in-dwelling electrodes. A metal coil electrode is placed on the external surface of the scalp and used to induce synchronous neuron firing in the adjacent cortex. This synchronous firing can thus mimic stimulation of the cortex using implanted electrodes.

Cortical Stimulation in an Animal Model of Parkinson's Disease

In view of the results described above, the inventors performed further experiments in two rats with 6-hydroxydopamine (6-OHDA) lesions of midbrain dopamine neurons, an established rodent model of Parkinson's disease[78, 79]. For recordings, rats were anaesthetised with urethane (1.3 gkg$^{-1}$), and supplementary doses of ketamine (30 mgkg$^{-1}$) and xylazine (3 mgkg$^{-1}$)[46, 77]. Note that the stereotyped LFP evoked in the subthalamic nucleus in control rats is relatively resistant to urethane anaesthesia[77].

Unilateral 6-OHDA lesions of dopamine neurons were induced according to a previously described protocol[46] and successful and widespread lesions were identified by standard behavioural tests[46]. The resultant chronic loss of dopamine means that the '6-OHDA-lesioned rat' is a good animal model of Parkinson's disease. Local field potentials were evoked in the brain in response to repeated (at 0.67 Hz) electrical stimulation (300-600 μA) of the somatomotor cortex[77]. To date, studies of basal ganglia function have used microelectrodes that have a single recording contact, and thus, it has been assumed that any differences between LFPs recorded at different depths are fixed over time. To address this issue directly, the inventors simultaneously recorded LFPs evoked above, in and below the subthalamic nucleus, along its length, using 'state-of-the-art' silicon probes[76]. Each probe has 16 recording contacts, with a centre-to-centre separation of 100 μm, arranged in a linear array.

Figure 10:
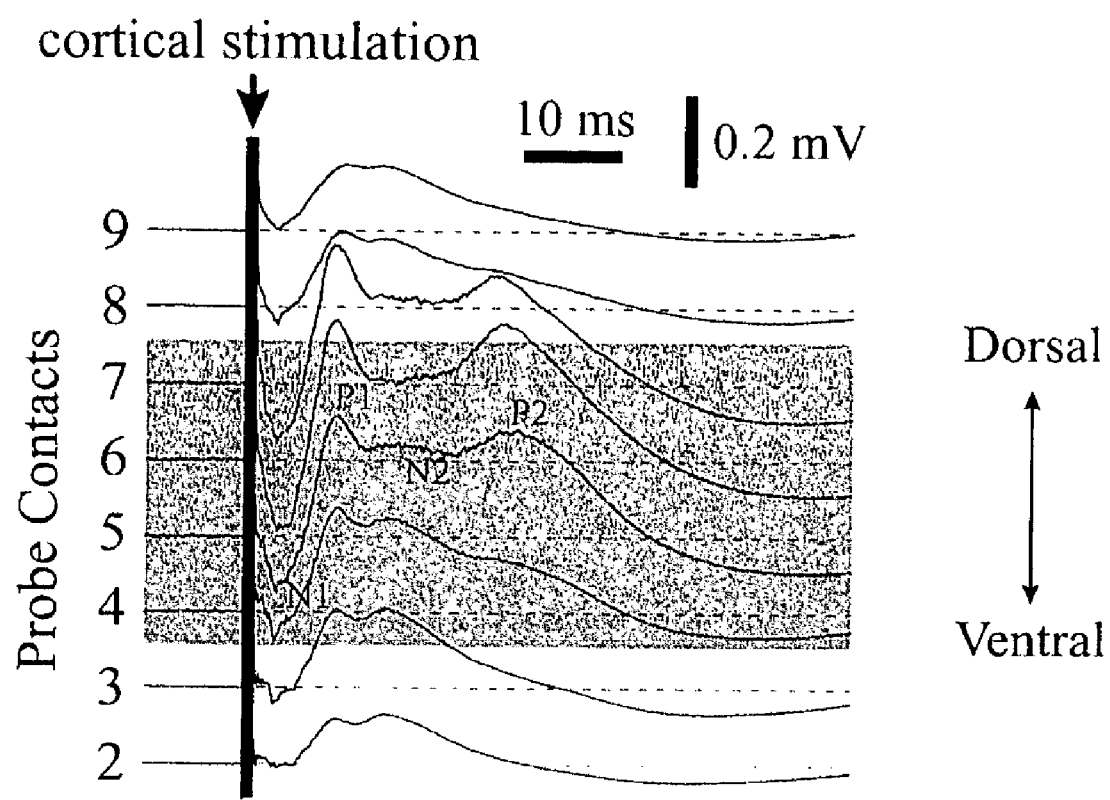
FIG. 10. Simultaneous recordings of local field potentials evoked in and around the subthalamic nucleus by electrical stimulation of ipsilateral somatomotor cortex in a 6-hydroxydopamine-lesioned rat. Traces represent averages of local field potentials evoked in response to 200 cortical stimuli. Grey box denotes approximate location of the subthalamic nucleus, as verified by histological analysis. Recording contacts 2-9 on the silicon probe are each separated by 100 µm. Dashed lines represent the isopotential (0 mV) at each recording contact. Note the emergence of characteristic negative (N1 and N2) and positive (P1 and P2) deflections in local field potentials recorded within the subthalamic nucleus only ($3^{rd}$, $4^{th}$ and $5^{th}$ traces, counting down from the top).

As can be seen in FIG. 10, stereotypical LFPs, consisting of a series of negative and positive voltage deflections, were indeed evoked in the subthalamic nucleus of the 6-OHDA-lesioned rats. However, these LFPs were not observed above or below the subthalamic nucleus. Furthermore, characteristic LFPs were only evoked in the rostral portion of the subthalamic nucleus and were similar in nature to those LFPs evoked in control rats[77].

These recordings are significant in that they further indicate that focal and distinctive local field potentials evoked in response to cortical stimulation can be used to identify the subthalamic nucleus, and specific domains within it, in the parkinsonian state. This data confirms that measurement of characteristic field potentials has clinical relevance in locating the position of selected neural centres and in directing an electrode to a position in the neural centre in the case where a pathological condition of that neural centre exists.

Acknowledgements

This work was supported by the Medical Research Council UK and the Brain Research Trust. P.J.M. holds a Fellowship by Examination at Magdalen College, Oxford. We are grateful to Drs. J. Csicsvari, T. Klausberger, M. Ungless, T. Aziz and J. Stein for their valuable comments. We also wish to thank L. Norman, B. Micklem and C. Francis.

Abbreviations

ABC, avidin-biotin peroxidase complex; BG, basal ganglia; CP, cerebral peduncle; ECG, electrocardiogram; EEG, electroencephalogram; GP, globus pallidus; LFP, local field potential; NS, neostriatum; PSTH, peristimulus time histogram; SD, standard deviation; STN, subthalamic nucleus; ZID, dorsal division of the zona incerta; ZIV, ventral division of the zona incerta.

REFERENCE

1. Afsharpour, S. (1985a) Light microscopic analysis of Golgi-impregnated rat subthalamic neurons. *J. Comp. Neurol.*, 236, 1-13.
2. Afsharpour, S. (1985b) Topographical projections of the cerebral cortex to the subthalamic nucleus. *J. Comp. Neurol.*, 236, 14-28.
3. Allers, K. A., Ruskin, D. N., Bergstrom, D. A., Freeman, L. E., Ghazi, L. J., Tierney, P. L. & Walters, J. R. (2002) Multisecond periodicities in basal ganglia firing rates correlate with theta bursts in transcortical and hippocampal EEG. *J. Neurophysiol.*, 87, 1118-1122.
4. Aoki, F., Fetz, E. E., Shupe, L., Lettich, E. & Ojemann, G. A. (1999) Increased gamma-range activity in human sensorimotor cortex during performance of visuomotor tasks. *Clin. Neurophysiol.*, 110, 524-537.
5. Bergman, H., Feingold, A., Nini, A., Raz, A., Slovin, H., Abeles, M. & Vaadia, E. (1998) Physiological aspects of information processing in the basal ganglia of normal and parkinsonian primates. *Trends Neurosci.*, 21, 32-38.
6. Bevan, M. D., Francis, C. M. & Bolam, J. P. (1995) The glutamate-enriched cortical and thalamic input to neurons in the subthalamic nucleus of the rat: convergence with GABA-positive terminals. *J. Comp. Neurol.*, 361, 491-511. 2829
7. Bevan, M. D., Magill, P. J., Terman, D., Bolam, J. P. & Wilson, C. J. (2002) Move to the rhythm: oscillations in the subthalamic nucleus-external globus pallidus network. *Trends Neurosci.*, 25, 525-531.
8. Bolam, J. P. (Ed) (1992) *Experimental Neuroanatomy*. Oxford University Press, Oxford.
9. Bolam, J. P., Magill, P. J. & Bevan, M. D. (2002) The functional organisation of the basal ganglia: New insights from anatomical and physiological analyses. In Nicholson, L. & Faull, R. (eds), *Basal Ganglia VII*. Kluwer Academic Publishing, pp. 371-378.
10. Boraud, T., Bezard, E., Bioulac, B. & Gross, C. E. (2002) From single extracellular unit recording in experimental and human Parkinsonism to the development of a functional concept of the role played by the basal ganglia in motor control. *Prog. Neurobiol.*, 66, 265-283.
11. Brown, P., Oliviero, A., Mazzone, P., Insola, A., Tonali, P. & Di Lazzaro, V. (2001) Dopamine dependency of oscillations between subthalamic nucleus and pallidum in Parkinson's disease. *J. Neurosci.*, 21, 1033-1038.
12. Brown, P., Kupsch, A., Magill, P. J., Sharott, A., Harnack, D. & Meissner, W. (2002) Oscillatory local field potentials recorded from the subthalamic nucleus of the alert rat. *Exp. Neurol.*, 177, 581-585.
13. Brown, P. (2003) Oscillatory nature of human basal ganglia activity: relationship to the pathophysiology of Parkinson's disease. *Mov. Disord.*, 18, 357-363.
14. Canteras, N. S., Shammah-Lagnado, S. J., Silva, B. A. & Ricardo, J. A. (1990) Afferent connections of the subthalamic nucleus: a combined retrograde and anterograde horseradish peroxidase study in the rat. *Brain Res.*, 513, 43-59.
15. Cassidy, M., Mazzone, P., Oliviero, A., Insola, A., Tonali, P., Di Lazzaro, V. & Brown, P. (2002) Movement-related changes in synchronization in the human basal ganglia. *Brain*, 125, 1235-1246.
16. Chabardès, S., Kahane, P., Minotti, L., Koudsie, A., Hirsch, E. & Benabid, A. L. (2002) Deep brain stimulation in epilepsy with particular reference to the subthalamic nucleus. *Epilepsy Disord.*, 4(Suppl 3), S82-S93.
17. DeLong, M. R. (1990) Primate models of movement disorders of basal ganglia origin. *Trends Neurosci.*, 13, 281-285.
18. Dinner, D. S., Neme, S., Nair, D., Montgomery, E. B. Jr., Baker, K. B., Rezai. A. & Luders, H. O. (2002) EEG and evoked potential recording from the subthalamic nucleus for deep brain stimulation of intractable epilepsy. *Clin. Neurophysiol.*, 113, 1391-1402.
19. Donoghue, J. P. & Wise, S. P. (1982) The motor cortex of the rat: cytoarchitecture and microstimulation mapping. *J. Comp. Neurol.*, 212, 76-88. 3031

20. Donoghue, J. P. & Parham, C. (1983) Afferent connections of the lateral agranular field of the rat motor cortex. *J. Comp. Neurol.*, 217, 390-404.
21. Donoghue, J. P., Sanes, J. N., Hastopoulos, N. G. & Gaál, G. (1998) Neural discharge and local field potential oscillations in primate motor cortex during voluntary movements. *J. Neurophysiol.*, 79, 159-173.
22. Engel, A. K. & Singer, W. (2001) Temporal binding and the neural correlates of sensory awareness. *Trends Cog. Sci.*, 5, 16-25.
23. Engel, K., Fries, P. & Singer, W. (2001) Dynamic Predictions: oscillations and synchrony in top-down processing. *Nature Rev. Neurosci.*, 2, 704-716.
24. Ellaway, P. H. (1978) Cumulative sum technique and its application to the analysis of peristimlus time histograms. *J. Physiol.*, 45, 320-304.
25. Fujimoto, K. & Kita, H. (1993) Response characteristics of subthalamic neurons to the stimulation of the sensorimotor cortex in the rat. *Brain Res.*, 609, 185-192.
26. Gerfen, C. R. & Wilson, C. J. (1996) The basal ganglia. In Swanson, L. W., Björklund, A. & Hökfelt, T. (eds), *Handbook of chemical neuroanatomy* 12: *integrated systems of the CNS III*. Elsevier, London, pp. 371-468.
27. Graybiel, A. M. (1995) Building action repertoires: memory and learning functions of the basal ganglia. *Curr. Opin. Neurobiol.*, 5, 733-741.
28. Harris, K. D., Csicsvari. J., Hirase, H., Dragoi, G. & Buzsáki, G. (2003) Organization of cell assemblies in the hippocampus. *Nature*, 424, 552-556.
29. Horikawa, K. & Armstrong, W. E. (1991) A biocytin-containing compound N-(2-aminoethyl)biotinimide for intracellular labeling and neuronal tracing studies: comparison with biocytin. *J. Neurosci. Methods*, 37, 141-150.
30. Hubbard, J. I., Llinás, R. & Quastel, D. M. J. (1969) Extracellular field potentials in the central nervous system. In *Electrophysiological analysis of synaptic transmission*, Edward Arnold (Publishers) Ltd., London, pp. 265-293.
31. Kita, H., Chang, H. T. & Kitai, S. T. (1983) The morphology of intracellularly labeled rat subthalamic neurons: a light microscopic analysis. *J. Comp. Neurol.*, 215, 245-257.
31a. Kita, H. & Armstrong, W. E. (1991) A biocytin-containing compound N-(2-aminoethyl)biotinimide for intracellular labeling and neuronal tracing studies: comparison with biocytin. *J. Neurosci. Methods*, 37, 141-150.
32. Kita, H. & Kitai, S. T. (1991) Intracellular study of rat globus pallidus neurons: membrane properties and responses to neostriatal, subthalamic and nigral stimulation. *Brain Res.*, 564, 296-305.
33. Kitai, S. T. & Deniau, J. M. (1981) Cortical inputs to the subthalamus: intracellular analysis. *Brain Res.*, 214, 411-415.
34. Klostermann, F., Vesper, J. & Curio, G. (2003) Identification of target areas for deep brain stimulation in human basal ganglia substructures based on median nerve sensory evoked potential criteria. *J Neurol Neurosurg Psychiatry* 74, 1031-1035.
35. Kolomiets, B. P., Deniau, J. M., Mailly, P., Ménétrey, A., Glowinski, J. & Thierry, A. M. (2001) Segregation and convergence of information flow through the cortico-subthalamic pathways. *J. Neurosci.*, 21, 5764-5772.
36. Kristeva-Feige, R., Feige, B., Makeig, S., Ross, B. & Elbert, T. (1993) Oscillatory brain activity during a motor task. *Neuroreport*, 4, 1291-1294.
37. Kumar, R., Chen, R. & Ashby, P. (1999) Safety of transcranial magnetic stimulation in patients with implanted deep brain stimulators. *Mov. Disord.*, 14, 157-158.
38. Kumar, R., Lozano, A. M., Kim, Y. J., Hutchison, W. D., Sime, E., Halket, E. & Lang, A. E. (1998) Double-blind evaluation of subthalamic nucleus deep brain stimulation in advanced Parkinson's disease. *Neurology*, 51, 850-855.
39. Levy, R., Ashby, P., Hutchison, W. D., Lang, A. E., Lozano, A. M. & Dostrovsky, J. O. (2002) Dependence of subthalamic nucleus oscillations on movement and dopamine in Parkinson's disease. *Brain*, 125, 1196-1209.
40. Limousin, P., Krack, P., Pollak, P., Benazzouz, A., Ardouin, C., Hoffmann, D. & Benabid, A. L. (1998) Electrical stimulation of the subthalamic nucleus in advanced Parkinson's disease. *N. Engl. J. Med.*, 339, 1105-1111.
41. Liu, X., Ford-Dunn, H. L., Hayward, G. N., Nandi, D., Miall, R. C., Aziz, T. Z. & Stein. J. (2002) The oscillatory activity in the Parkinsonian subthalamic nucleus investigated using the macro-electrodes for deep brain stimulation. *Clin. Neurophysiol.*, 113, 1667-1672.
42. Liu, X., Rowe, J., Nandi, D., Hayward, G., Parkin, S., Stein, J. & Aziz, T. (2001) Localisation of the Subthalamic Nucleus Using Radionics Image Fusion™ and Steroplan™ Combined with Field Potential Recording. *Stereotact Funct Neurosurg.*, 76, 63-73.
43. Loddenkemper, T., Pan, A., Neme, S., Baker, K. B., Rezai, A. R., Dinner, D. S., Montgomery, E. B. Jr. & Luders, H. O. (2001) Deep brain stimulation in epilepsy. *J. Clin. Neurophysiol.*, 18, 514-532.
44. MacKay, W. A. (1997) Synchronised neuronal oscillations and their role in motor processes. *Trends Cog. Sci.*, 1, 176-183.
45. Magill, P. J., Bolam, J. P. & Bevan, M. D. (2000) Relationship of activity in the subthalamic nucleus-globus pallidus network to cortical electroencephalogram. *J. Neurosci.*, 20, 820-833.
46. Magill, P. J., Bolam, J. P. & Bevan, M. D. (2001) Dopamine regulates the impact of the cerebral cortex on the subthalamic nucleus-globus pallidus network. *Neuroscience*, 106, 313-330.
47. Marsden, J. F., Limousin-Dowsey. P., Ashby, P., Pollak, P. & Brown, P. (2001) Subthalamic nucleus, sensorimotor cortex and muscle interrelationships in Parkinson's disease. *Brain*, 124, 378-388.
48. Maurice, N., Deniau, J. M., Glowinski, J. & Thierry, A. M. (1998) Relationships between the prefrontal cortex and the basal ganglia in the rat: Physiology of the corticosubthalamic circuits. *J. Neurosci.*, 18, 9539-9546.
49. Maurice, N., Deniau, J. M., Glowinski, J. & Thierry, A. M. (1999) Relationships between the prefrontal cortex and the basal ganglia in the rat: Physiology of the cortico-nigral circuits. *J. Neurosci.*, 19, 4674-4681.
50. McCormick, D. A. & Bal, T. (1997) Sleep and arousal: thalamocortical mechanisms. *Annu. Rev. Neurosci.*, 20, 185-215.
51. Mink, J. W. (1996) The basal ganglia: focused selection and inhibition of competing motor programs. *Prog. Neurobiol.*, 50, 381-425.
52. Mitrofanis, J. & Mikuletic, L. (1999) Organisation of the cortical projection to the zona incerta of the thalamus. *J. Comp. Neurol.*, 412, 173-185.
53. Mitzdorf, U. (1985) Current-source density method and application in cat cerebral cortex: investigation of evoked potentials and EEG phenomena. *Physiol. Rev.*, 65, 37-100.
54. Murthy, V. N. & Fetz, E. E. (1992) Coherent 25- and 35-Hz oscillations in the sensorimotor cortex of awake behaving monkeys. *Proc. Natl. Acad. Sci. USA*, 89, 5670-5674.

55. Murthy, V. N. & Fetz, E. E. (1996) Synchronization of neurons during local field potential oscillations in sensorimotor cortex of awake monkeys. *J. Neurophysiol.*, 76, 3968-3982.

56. Nambu, A., Tokuno, H., Hamada, I., Kita, H., Imanishi, M., Akazawa, T., Ikeuchi, Y. & Hasegawa, N. (2000) Excitatory cortical inputs to pallidal neurons via the subthalamic nucleus in the monkey. *J. Neurophysiol.*, 84, 289-300.

57. Nambu, A., Tokuno, H. & Takada, M. (2002) Functional significance of the cortico-subthalamo-pallidal 'hyperdirect' pathway. *Neurosci. Res.*, 43, 111-117.

58. Orieux, G., François, C., Féger, J. & Hirsch, E. C. (2002) Consequences of dopaminergic denervation on the metabolic activity of the cortical neurons projecting to the subthalamic nucleus in the rat. *J. Neurosci.*, 22, 8762-8770.

59. Paxinos, G. & Watson, C. (1986) *The rat brain in stereotaxic coordinates* (2nd Edn). Academic Press, Sydney, Aus.

60. Priori, A., Egidi, M., Pesenti, A., Rohr, M., Rampini, P., Locatelli, M., Tamma, F., Caputo, E., Chiesa, V. & Barbieri, S. (2003) Do intraoperative microrecordings improve subthalamic nucleus targeting in stereotactic neurosurgery for Parkinson's disease? *J. Neurosurg. Sci.*, 47, 56-60.

61. Roelfsema, P. R., Engel, A. K., König, P. & Singer, W. (1997) Visuomotor integration is associated with zero time-lag synchronization among cortical areas. *Nature*, 385, 157-161.

62. Rouzaire-Dubois, B. & Scarnati, E. (1987) Pharmacological study of the cortical-induced excitation of subthalamic nucleus neurons in the rat: evidence for amino acids as putative neurotransmitters. *Neuroscience*, 21, 429-440.

63. Ryan, L. J. & Clark, K. B. (1991) The role of the subthalamic nucleus in the response of globus pallidus neurons to stimulation of the prelimbic and agranular frontal cortices in rats. *Exp. Brain Res.*, 86, 641-651.

64. Ryan, L. J. & Clark, K. B. (1992) Alteration of neuronal responses in the subthalamic nucleus following globus pallidus and neostriatal lesions in rats. *Brain Res. Bull.*, 29, 319-327.

65. Ryan, L. J., Sanders, D. J. & Clark, K. B. (1992) Auto- and cross-correlation analysis of subthalamic nucleus neuronal activity in neostriatal- and globus pallidal-lesioned rats. *Brain Res.*, 583, 253-261.

66. Saint-Cyr, J. A., Hoque, T., Pereira, L. C., Dostrovsky, J. O., Hutchison, W. D., Mikulis, D. J., Abosch, A., Sime, E., Lang, A. E. & Lozano, A M. (2002) Localization of clinically effective stimulating electrodes in the human subthalamic nucleus on magnetic resonance imaging. *J. Neurosurg.*, 97, 1152-1166.

67. Smith, Y., Bevan, M. D., Shink, E. & Bolam, J. P. (1998) Microcircuitry of the direct and indirect pathways of the basal ganglia. *Neuroscience*, 86, 353-387.

68. Starr, P. A. (2002) Placement of deep brain stimulators into the subthalamic nucleus or Globus pallidus internus: technical approach. *Stereotact. Funct. Neurosurg.*, 79, 118-145.

69. Steriade, M. (2000) Corticothalamic resonance, states of vigilance and mentation. *Neuroscience*, 101, 243-76.

70. Voges, J., Volkmann, J., Allert, N., Lehrke, R., Koulousakis, A., Freund, H. J. & Sturm, V. (2002) Bilateral high-frequency stimulation in the subthalamic nucleus for the treatment of Parkinson disease: correlation of therapeutic effect with anatomical electrode position. *J. Neurosurg.*, 96, 269-279.

71. Wichmann, T. & DeLong, M. R. (1996) Functional and pathophysiological models of the basal ganglia. *Curr. Opin. Neurobiol.*, 6, 751-758.

72. Wichmann, T., Kliem, M, A. & Soares, J. (2001) Correlation between neuronal discharge in the basal ganglia and EEG in normal and parkinsonian primates. *Soc. Neuorsci. Abstr.*, 31, 749. 23.

73. Williams, D., Tijssen, M., Van Bruggen. G., Bosch, A., Insola, A., Di Lazzaro, V., Mazzone, P., Oliviero, A., Quartarone, A., Speelman, H. & Brown, P. (2002) Dopamine-dependent changes in the functional connectivity between basal ganglia and cerebral cortex in humans. *Brain*, 125, 1558-1569.

74. Williams, D., Kuhn, A., Kupsch, A., Tijssen, M., Van Bruggen, G., Speelman, H., Hotton, G., Yarrow, K. & Brown P (2003) Behavioural cues are associated with modulations of synchronous oscillations in the human subthalamic nucleus. *Brain*, In press.

75. Yelnik, J. & Percheron, G. (1979) Subthalamic neurons in primates: a quantitative and comparative analysis. *Neuroscience*, 4, 1717-1743.

76. Buzsaki G (2004) Large-scale recording of neuronal ensembles. *Nat Neurosci* 7:446-451.

77. Magill P J, Sharott A, Bevan M D, Brown P, Bolam J P (2004) Synchronous unit activity and local field potentials evoked in the subthalamic nucleus by cortical stimulation. *J Neurophysiol* 92:700-714.

78. Schwarting R K W, Huston J P (1996a) Unilateral 6-hydroxydopamine lesions of meso-striatal dopamine neurons and their physiological sequelae. *Prog Neurobiol* 49:215-266.

79. Schwarting R K W, Huston J P (1996b) The unilateral 6-hydroxydopamine lesion model in behavioral brain research. Analysis of functional deficits, recovery and treatments. *Prog Neurobiol* 50:275-331.

The invention claimed is:

1. A method of locating the position of the subthalamic nucleus in the central nervous system of an animal comprising the steps of:
   a) stimulating neurons at a first central nervous system position by applying a stimulus to the brain;
   b) measuring the field potential evoked at a second central nervous system position;
   c) comparing the evoked field potential against a known characteristic evoked field potential from the subthalamic nucleus resulting from stimulation of the brain; and
   d) locating the subthalamic nucleus with the comparison in step c.

2. The method of claim 1 further comprising repeating steps ac for one or a plurality of cycles, wherein in each subsequent cycle the position of measurement in step b) is adjusted, until the evoked field potential corresponds to said known evoked field potential.

3. The method of claim 1 wherein steps a) and b) are performed simultaneously.

4. The method of claim 1 wherein the first central nervous system position is in the cerebral cortex.

5. The method of claim 1 wherein the first central nervous system position is in the frontal cortex.

6. The method of claim 1 wherein the first central nervous system position is in the pre-frontal cortex.

7. The method of claim 1 wherein the first central nervous system position is in the temporal cortex.

8. The method of claim 1 wherein the second central nervous system position is in the basal ganglia or ventral thalamus.

9. The method of claim 1 wherein the second central nervous system position is selected from the group consisting of:
   i) the subthalamic nucleus;
   ii) the rostral subthalamic nucleus;
   iii) the caudal subthalamic nucleus;
   iv) the ventral intermediate nucleus;
   v) the zona incerta;
   vi) the globus pallidus; or
   vii) the substantia nigra.

10. The method of claim 1 wherein the animal is a human.

11. The method of claim 1 wherein the measurement of field potential is taken by at least one electrode inserted into the central nervous system.

12. The method of claim 11 wherein said electrode is a therapeutic electrode.

13. The method of claim 11 wherein said electrode is a deep brain stimulation electrode.

14. The method of claim 1 wherein the stimulation of step a) is achieved by transcranial electrical stimulation or transcranial magnetic stimulation.

15. The method of claim 1, wherein said stimulus is applied on the brain, in the brain, or over the brain.

16. The method of claim 1, wherein said stimulus is applied with an electrode positioned on the brain, in the brain, or over the brain.

17. A method of treating a patient in need of treatment by electrical stimulation of the subthalamic nucleus comprising positioning a stimulating electrode at the subthalamic nucleus, wherein the position of the subthalamic nucleus in the central nervous system of the patient is determined by:
   a) the method of claim 1; and
   b) treating by electrically stimulating the subthalamic nucleus.

18. The method of claim 17 wherein said electrical stimulation is a deep brain electrical stimulation.

19. A method of treating a patient in need of treatment by electrocoagulation of the subthalamic nucleus comprising positioning an electrocoagulation electrode at the subthalamic nucleus, wherein the position of the subthalamic nucleus in the central nervous system of the patient is determined by:
   a) the method of claim 1; and
   b) treating by electrocoagulating the subthalamic nucleus.

20. A method of treating a patient exhibiting a Parkinson's disease, or Parkinson's disease-like, motor dysfunction by electrical stimulation or electrocoagulation of the subthalamic nucleus comprising positioning an electrode at a position in the subthalamic nucleus, wherein the position of the subthalamic nucleus in the central nervous system is determined by:
   a) the method of claim 1; and
   b) treating by electrically stimulating or electrocoagulating the subthalamic nucleus.

21. A method of treating a patient exhibiting epileptic, or epilepsy-related, dysfunction by electrical stimulation or electrocoagulation of the subthalamic nucleus comprising positioning an electrode at a position in the subthalamic nucleus, wherein the position of the subthalamic nucleus in the central nervous system is determined by:
   a) the method of claim 1; and
   b) treating by electrically stimulating or electrocoagulating the subthalamic nucleus.

22. A method of directing an electrode to a position in the subthalamic nucleus in the central nervous system of an animal comprising the steps of:
   i) stimulating neurons at a first central nervous system position by applying a stimulus to the brain;
   ii) measuring the field potential evoked at an electrode located at a second central nervous system position;
   iii) comparing the evoked field potential against a known characteristic evoked field potential from the subthalamic nucleus, and
   iv) repeating steps i-iii for one or a plurality of cycles until the evoked field potential corresponds to said known evoked field potential,
   wherein between subsequent cycles the evoked field potential is analysed and the position of measurement in step ii) is adjusted to optimise the correspondence between the evoked and known field potentials in the subsequent cycle.

23. A method of locating the position of the subthalamic nucleus in the central nervous system of an animal comprising the steps of:
   a) stimulating neurons of the cerebral cortex;
   b) measuring the field potential evoked at a position in the brain;
   c) comparing the evoked field potential against a known characteristic evoked field potential from the subthalamic nucleus resulting from stimulation of the cerebral cortex; and d) locating the subthalamic nucleus with the comparison in step c.

24. The method of claim 23 wherein the animal is a human.

25. A method of locating the position of the subthalamic nucleus of an animal comprising the steps of:
   a) stimulating neurons at a first central nervous system position;
   b) measuring the field potential evoked at a second central nervous system position;
   c) comparing the evoked field potential against a known characteristic evoked field potential from the subthalamic nucleus resulting from stimulation of the first central nervous system position; and d) locating the subthalamic nucleus with the comparison in step c.

* * * * *

UNITED STATES PATENT AND TRADEMARK OFFICE
CERTIFICATE OF CORRECTION

PATENT NO. : 7,582,062 B2  Page 1 of 1
APPLICATION NO. : 10/939851
DATED : September 1, 2009
INVENTOR(S) : Magill et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 838 days.

Signed and Sealed this

Fourteenth Day of September, 2010

David J. Kappos
*Director of the United States Patent and Trademark Office*